US011523762B2

(12) United States Patent
Ruppersberg et al.

(10) Patent No.: US 11,523,762 B2
(45) Date of Patent: Dec. 13, 2022

(54) ELECTROPHYSIOLOGICAL MAPPING CATHETER

(71) Applicant: Ablacon Inc., Wheat Ridge, CO (US)

(72) Inventors: Peter Ruppersberg, Blonay (CH); Peter Jacobs, St. Louis Park, MN (US)

(73) Assignee: Ablacon Inc., Wheat Ridge, CO (US)

( * ) Notice: Subject to any disclaimer, the term of this patent is extended or adjusted under 35 U.S.C. 154(b) by 425 days.

(21) Appl. No.: 16/691,368

(22) Filed: Nov. 21, 2019

(65) Prior Publication Data

US 2020/0121208 A1 Apr. 23, 2020

Related U.S. Application Data

(63) Continuation-in-part of application No. 15/793,594, filed on Oct. 25, 2017, now Pat. No. 10,813,590.

(60) Provisional application No. 62/828,069, filed on Apr. 2, 2019, provisional application No. 62/770,697, filed on Nov. 21, 2018.

(51) Int. Cl.
*A61M 25/00* (2006.01)
*A61B 5/287* (2021.01)
*A61B 5/00* (2006.01)

(52) U.S. Cl.
CPC ............ *A61B 5/287* (2021.01); *A61B 5/6858* (2013.01); *A61M 25/001* (2013.01); *A61M 25/0074* (2013.01); *A61M 2205/0216* (2013.01); *A61M 2205/0233* (2013.01); *A61M 2205/0266* (2013.01); *A61M 2205/0283* (2013.01); *A61M 2205/3303* (2013.01); *A61M 2230/04* (2013.01)

(58) Field of Classification Search
CPC .................. A61B 5/6859; A61B 5/287; A61B 2018/00351; A61B 2018/00267; A61B 2018/00214; A61B 5/6858; A61B 5/6867; A61B 5/6869
See application file for complete search history.

(56) References Cited

U.S. PATENT DOCUMENTS

2017/0164858 A1* 6/2017 Basu .................... A61B 5/6859

* cited by examiner

*Primary Examiner* — Jon Eric C Morales
(74) *Attorney, Agent, or Firm* — Woods Patent Law, P.C.

(57) ABSTRACT

Disclosed are various examples and embodiments of a cardiac mapping catheter configured for electrophysiological (EP) mapping and suitable for intravascular insertion in a patient's heart, and methods of making same. The cardiac mapping catheter comprises a plurality support arms having electrodes disposed thereon. Various configurations of the cardiac mapping catheter are described and disclosed which provide improved spatial resolution and sensing of EP signals acquired from inside a patient's heart.

20 Claims, 15 Drawing Sheets

ELECTROPHYSIOLOGICAL MAPPING CATHETER

RELATED APPLICATIONS

This application is related to, and claims priority and other benefits from: (a) U.S. Provisional Patent Application Ser. No. 62/770,697 entitled "Electrophysiological Mapping Catheter" to Ruppersberg filed Nov. 21, 2018 (hereafter "the '697 patent application"), and (b) U.S. Provisional Patent Application Ser. No. 62/828,069 entitled "Methods, Systems, Devices and Components for Electrophysiological Mapping Catheters" to Ruppersberg filed Apr. 2, 2019 (hereafter "the '069 patent application"). This application is also related to, and claims priority and other benefits from, U.S. Provisional Patent Application Ser. No. 62/414,183 entitled "Improved Electrophysiological Mapping Catheter" to Ruppersberg filed Oct. 28, 2016 (hereafter "the '183 patent application") through U.S. Utility patent application Ser. No. 15/793,594 entitled "Electrophysiological Mapping Catheter" filed Oct. 25, 2017 (now published as U.S. Patent Publication No. US 2018/0116595; hereafter "the '594 patent application"). This application is also a continuation-in-part of U.S. Utility patent application Ser. No. 15/793,594 '183 (or the '594 patent application). The '697, '069, '183, and '594 patent applications are incorporated by reference herein, each in its respective entirety.

FIELD OF THE INVENTION

Various embodiments described and disclosed herein relate to the field of medicine generally, and more particularly to electrophysiological (EP) mapping catheters employed to diagnose and treat cardiac rhythm disorders in a patient's heart.

BACKGROUND

Elongated medical devices suitable for intravascular insertion, such as catheters, especially ablation catheters, and guide wires for guiding catheters through vessels, organs or other body cavities are often employed in the treatment of atrial fibrillation (Afib). Atrial fibrillation is the most frequent arrhythmic disorder of the heart. Blood clotting occurring in the fibrillating atria is one main cause of stroke. Afib is also one of the most important disorders associated with a high risk of fatality. The cause of Afib has been subject to intensive scientific investigations and is largely understood. In most patients, the pulmonary veins draining into the left atrium are the sources of rapid arrhythmic action potentials which trigger circular excitation patterns (rotors) in the left atrium that induce a high frequency fibrillation through their re-entry mechanism. Those rotors have the character of small action potential cyclones of 2 to 3 $cm^2$ in size. The likelihood of occurrence of those rotors and the frequency of pathological action potential generation in the pulmonary veins increases with fibrotic structural changes and certain modifications of ion channel expression patterns in atrial cells with age.

The only potentially curative treatments for Afib are open heart surgery or cardiac ablation employing a catheter for those parts of the atrial wall tissue which originate, transmit or maintain the pathologic excitation circles.

Open heart surgery and catheter ablation are limited by potentially fatal and/or severe side effects associated with either procedure. When the integrity of the atrial wall is destroyed by excessive ablation, perforations of the atrial wall into the pericardium or fistulas into the esophagus can result in severe to deadly outcomes. The alteration of endocardial cells on the intra-cardiac surfaces can also initiate clotting in the treated atrium, which may lead to deadly strokes. That is why ablation procedures require the use of anticoagulation techniques. Last but not least, if the intensity of the ablation is kept too low to avoid the foregoing side effects, in many cases the therapeutic effect is insufficient and patients are often provided with success rates of only 50-70%.

To improve the situation, mapping catheters are often used first to identify circular excitation patterns (rotors) in the left atrium. After rotors have been identified, force sensing catheters are used that allow improved control of cardiac ablation catheter positions and pressures, which permits the intensity of tissue ablation to be better modulated and controlled. Further, water irrigation is often employed to keep endothelial tissue free of lesions during the ablation procedure, and micro-calorimetric sensors may be employed to measure and control the amount of heat delivered to the tissue during the ablation procedure.

U.S. Pat. No. 8,364,234 discloses a system for sensing multiple local electric voltages from endocardial surface of a heart. The system includes a first elongate tubular member; a basket assembly having a plurality of flexible splines for guiding a plurality of exposed electrodes, the splines having proximal portions, distal portions and medial portions therein between; a proximal anchor for securely affixing the proximal portions of the splines; the proximal anchor being secured at the distal end of the first elongate tubular member; a distal tip consisting essentially of means for only securely affixing the distal portions of the splines wherein at least some of the splines in the radially expanded non-spherical shape contain a distal outward bend disposed at the distal portion of the spline at a location near to the distal tip of the basket assembly to bend the splines back towards the proximal anchor. A disadvantage of this type of mapping system is the low resolution sometimes provided by the mapping electrode array, as the splines upon which the electrodes are mounted or attached tend to bunch or cluster when the endocardial surface of the patient's heart is contacted, thus reducing the area of the patient's heart that is sensed, and the spatial resolution provided, by the electrodes.

Laughner et, al. in JACC, CLINICAL ELECTROPHYSIOLOGY, 2016; 2(1):55-65. doi: 10.1016, conclude that known mapping basket catheters (NBC's) provide insufficient spatial resolution due to poor contact, demonstrate frequent bunching of basket splines, and possess inadequate electrode density to permit accurate detection of rotors near the equatorial electrodes of MBCs.

What is needed are improved means and methods of acquiring cardiac mapping data from inside a patient's heart using a cardiac mapping catheter, where improved spatial resolution of the electrodes when they are in contact with the patient's endocardium is provided.

SUMMARY

In one embodiment, there is provided a cardiac mapping catheter configured for electrophysiological mapping and suitable for intravascular insertion in a patient's heart, the catheter comprising a flexible elongated body having a distal portion with a distal end and a proximal portion, and an electrode assembly located at the distal portion, the electrode assembly comprising a plurality of support arms, each support arm having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition, where the plurality of support arms is arranged in a collapsed bundle, and a second expanded condition, where the plurality of support arms forms an expanded basket structure, at least one of two or more neighboring distal end parts and two or more neighboring proximal end parts being combined, attached to one another, or held together with one or more combining means, members or structures, and wherein the combining means, members or structures further are configured to act as or comprise at least one of stiffening, directionally biased, movement-limiting, rotation-limiting, and twisting-limiting means, members or structures, such stiffening means, members or structures being configured to prevent bunching and promote spacing apart of adjoining support arms when the expanded basket structure is deployed inside a patient's heart in the expanded second condition.

In another embodiment, there is provided a method of making a cardiac mapping catheter configured for electrophysiological mapping and suitable for intravascular insertion in a patient's heart, the method comprising forming a flexible elongated body having a distal portion with a distal end and a proximal portion, and forming an electrode assembly located at the distal portion, the electrode assembly comprising a plurality of support arms, each support arm having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition, where the plurality of support arms is arranged in a collapsed bundle, and a second expanded condition, where the plurality of support arms forms an expanded basket structure, at least one of two or more neighboring distal end parts and two or more neighboring proximal end parts being combined, attached to one another, or held together with one or more combining means, members or structures, wherein the combining means, members or structures further are configured to act as or comprise at least one of stiffening, directionally biased, movement-limiting rotation-limiting, and twisting-limiting means, members or structures, such stiffening means, members or structures being configured to prevent bunching and promote spacing apart of adjoining support arms when the plurality of support arms and the expanded basket structure is deployed inside a patient's heart in the expanded second condition.

In yet another embodiment, there is provided a cardiac mapping catheter configured for electrophysiological mapping and suitable for intravascular insertion in a patient's heart, the catheter comprising a flexible elongated body having a distal portion with a distal end and a proximal portion, and an electrode assembly located at the distal portion, the electrode assembly comprising a plurality of support arms comprising Nitinol or shape memory alloy splines, each spline having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition, where the plurality of support arms is arranged in a collapsed bundle, and a second expanded condition, where the plurality of support arms forms an expanded basket structure, wherein the Nitinol or shape memory splines are cut from a single sheet of Nitinol or shape memory alloy disposed or located on a flat or substantially flat surface during cutting, each spline being cut from the sheet such that at its proximal end part each spline terminates in an attachment member contiguous with the proximal end part of the spline, the attachment member being cut from the same sheet of Nitinol or shape memory alloy as the spline, wherein each spline is cut from the flat or substantially flat sheet such that between its proximal end part and its distal end part each spline forms a series of compound curves or arcs that curve first in a first general direction and then curve second in a second general direction opposite or partially opposite to or from the first direction, the distal end parts of the splines forming separate distal ends that are not connected to one another, the splines being nested together on the flat or substantially flat surface when the curves in the splines are being cut such that the splines are adjacent to one another and are separated from adjoining splines by continuous intervening spaces formed between the proximal end parts and the distal ends of the splines during cutting, the collar being configured, after cutting, to be joined, attached, or secured to the distal portion or distal end of the elongated body or to a distal tip of the basket structure, and further wherein after the splines have been formed from the sheet, after the attachment member has been attached to the distal portion or distal end of the elongated body, and after the distal ends of the splines have been attached or secured to the distal tip, the basket structure forms a series of spirally winding or spirally wrapping support arms when deployed in the second expanded condition, the basket structure and electrodes being configured to prevent bunching and promote spacing apart of adjoining support arms when the expanded basket structure is deployed inside a patient's heart in the expanded second condition.

In still another embodiment, there is provided a method of making a cardiac mapping catheter configured for electrophysiological mapping and suitable for intravascular insertion in a patient's heart, the catheter comprising a flexible elongated body having a distal portion with a distal end and a proximal portion, and an electrode assembly located at the distal portion, the electrode assembly comprising a plurality of support arms comprising Nitinol or shape memory alloy splines, each spline having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition, where the plurality of support arms is arranged in a collapsed bundle, and a second expanded condition, where the plurality of support arms forms an expanded basket structure, the method comprising cutting the Nitinol or shape memory splines from a single sheet of Nitinol or shape memory alloy disposed or located on a flat or substantially flat surface during cutting, cutting each spline from the sheet such that at its proximal end part each spline terminates in an attachment member contiguous with the proximal end part of the spline, cutting the collar from the same sheet of Nitinol or shape memory alloy as the spline, cutting each spline from the flat or substantially flat sheet such that between its proximal end part and its distal end part each spline forms a series of compound curves or arcs that curve first in a first general direction and then curve second in a second general direction opposite or partially opposite to or from the first direction, the distal end parts of the splines forming separate distal ends that are not connected to one another, the splines being nested together on the flat or substantially flat surface while the curves in the splines are being cut such that the splines are adjacent to one another and are separated from adjoining splines by continuous intervening spaces formed between the proximal end parts and the distal ends of the splines during cutting, and configuring the attachment member, after cutting, to be joined, attached, or secured to the distal portion or distal end of the elongated body or to a distal tip of the basket structure, wherein after the splines have been formed from the sheet, after the collar has been attached to the distal portion or distal end of the elongated body, and after the distal ends of the splines have been attached or secured to the distal tip, the basket structure forms a series of spirally winding or spirally wrapping support arms when deployed in the second expanded condition, the basket structure and electrodes being configured to prevent bunching and promote spacing apart of adjoining support arms when the expanded basket structure is deployed inside a patient's heart in the expanded second condition.

In a further embodiment, there is provided a cardiac mapping catheter configured for electrophysiological mapping and suitable for intravascular insertion in a patient's heart, the catheter comprising a flexible elongated body having a distal portion with a distal end and a proximal portion, and an electrode assembly located at the distal portion, the electrode assembly comprising a plurality of support arms comprising Nitinol or shape memory alloy splines, each spline having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition, where the plurality of support arms is arranged in a collapsed bundle, and a second expanded condition, where the plurality of support arms forms an expanded basket structure, wherein the Nitinol or shape memory alloy splines are cut from a single tube of Nitinol or shape memory alloy, each spline being formed or cut from the tube such that at its distal end part each spline terminates in a ring or collar contiguous with the distal end part of the spline, the ring or collar being cut from the same tube of Nitinol or shape memory alloy as the splines and forming a distal portion of the basket structure, the proximal end parts of the splines forming separate proximal ends that are not connected to one another after being cut from the tube, the proximal ends of the splines being configured, after cutting, to be joined, attached, or secured to the distal portion or distal end of the elongated body, and further wherein after the splines have been formed from the tube, and after the proximal ends of the splines have been attached or secured to the distal portion or the distal end part of the flexible elongated body, the basket structure comprises a plurality of outwardly bowing or curved splines when deployed in the second expanded condition.

In a still further embodiment, there is provided a method of making a cardiac mapping catheter configured for electrophysiological mapping and suitable for intravascular insertion in a patient's heart, the catheter comprising a flexible elongated body having a distal portion with a distal end and a proximal portion, and an electrode assembly located at the distal portion, the electrode assembly comprising a plurality of support arms comprising Nitinol or shape memory alloy splines, each spline having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition; where the plurality of support arms is arranged in a collapsed bundle, and a second expanded condition, where the plurality of support arms forms an expanded basket structure, the method comprising cutting the Nitinol splines from a single tube of Nitinol or shape memory alloy; cutting each spline from the tube such that at its distal end part each spline terminates in a collar or ring contiguous with the distal end part of the spline, the collar or ring being cut from the same tube of Nitinol or shape memory alloy as the splines; further cutting each spline from the tube such the proximal end parts of each spline not connected to one another; and joining, attaching, or securing the proximal end parts of the splines to the distal portion or distal end of the elongated body; wherein after the splines have been formed from the tube, after the proximal end parts of the splines have been joined, attached, or secured to the distal portion or distal end of the elongated body, the basket structure comprises a plurality of outwardly bowing or curved splines when deployed in the second expanded condition. Other embodiments are disclosed herein or will become apparent to those skilled in the art after having read and understood the claims, specification and drawings hereof.

BRIEF DESCRIPTION OF THE DRAWINGS

Different aspects of the various embodiments will become apparent from the following specification, drawings and claims in which:

FIG. 4a is an enlarged view of an area of the electrode assembly of the elongated medical device of FIG. 3a according to the marking IVa in FIG. 3a;

FIG. 4b is an enlarged view of an area of the electrode assembly of the elongated medical device of FIG. 3b according to the marking IVb in FIG. 3b;

FIG. 4c is an enlarged view of an area of an electrode assembly of a further embodiment of an elongated medical device;

FIG. 5a is an enlarged cut section through a pair of neighboring support arms according to the marking Va in FIG. 4a;

The drawings are not necessarily to scale. Like numbers refer to like parts or steps throughout the drawings.

DETAILED DESCRIPTIONS OF SOME EMBODIMENTS

Described herein are various embodiments of a cardiac mapping catheter, and associated components, systems and methods of making and using same.

Systems and methods configured to detect in a patient's heart a location of a source of at least one cardiac rhythm disorder are disclosed herein. In the following description, for the purposes of explanation, numerous specific details are set forth in order to provide a thorough understanding of example embodiments or aspects. It will be evident, however, to one skilled in the art that an example embodiment may be practiced without necessarily using all of the disclosed specific details.

In one embodiment, an elongated medical device is provided that is suitable for intravascular insertion, such as a catheter for exploration or treatment of a vessel, organ or other body cavity which includes an electrode assembly for electrophysiological mapping of cardiac or vessel areas or the like medical apparatus. The electrode assembly may be used to map circular excitation patterns (rotors), e.g., of the left atrium of the heart.

Figure 1:
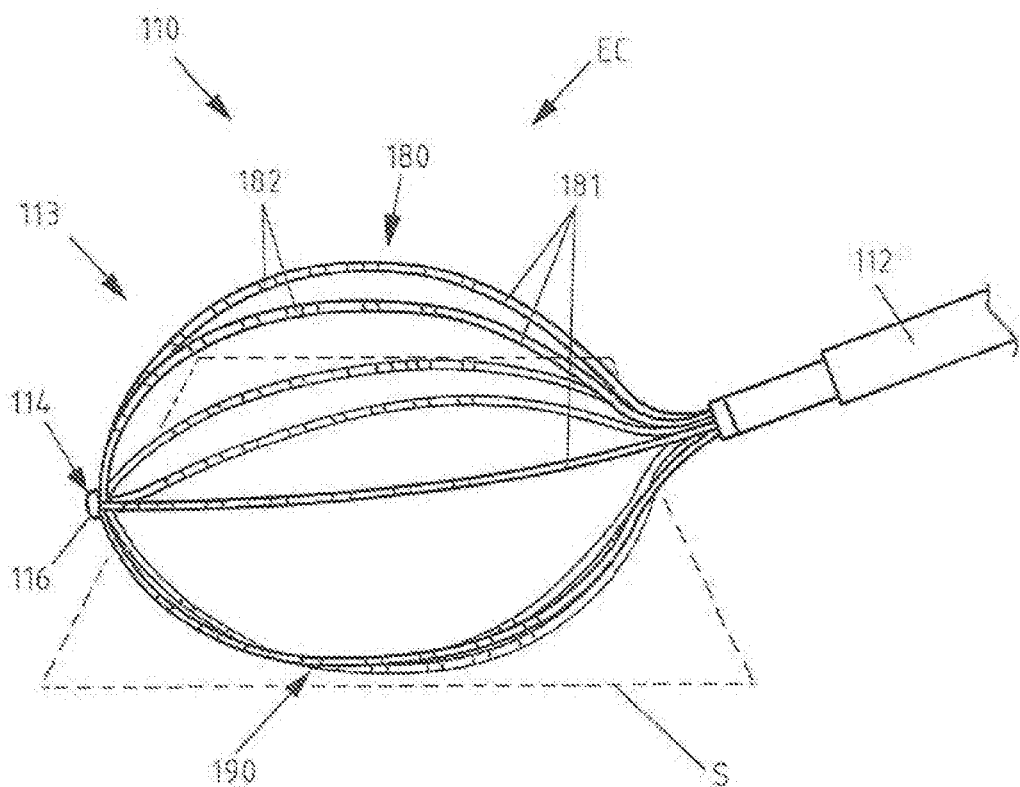
FIG. 1 is a schematic view of a basket type electrophysiological mapping catheter according to the prior art with an electrode assembly comprising support arms, the electrode assembly being in an expanded condition with a part of the support arms touching a surface.

Referring now to FIG. 1, there is illustrated a prior art elongated medical device 110 which is formed as a mapping catheter. The elongated medical device 110 comprises an elongated body 112, only a distal portion 113 of which is shown in FIG. 1. The elongated medical device 1101 mapping catheter comprises a basket type electrode assembly 180 that is displayed in FIG. 1 in its expanded condition (EC). The electrode assembly 180 comprises eight support arms 181 that carry electrodes 182. In the example shown, there are eight electrodes 182 arranged on each of the eight support arms 181. A tip 116 is disposed at a distal end 114 of the distal portion 113 of the elongated medical device 110. FIG. 1 depicts the situation where the basket type electrode assembly 180 with its support arms 181 touches a surface S, e.g., an organ or body surface such a patient's endocardium. As can be seen, the support arms 181 in contact with surface S bunch or accumulate on the surface S, and form a cluster 190 such that the 24 electrodes of the affected three support arms 181 effectively act, by way of example, as only 8 electrodes, as in the example of FIG. 1 the 24 electrodes of the three support arms are bunched together to form eight clusters, each cluster having three electrodes associated therewith. Due to such clustering, the spatial resolution of the electrodes is reduced significantly.

Figure 2:
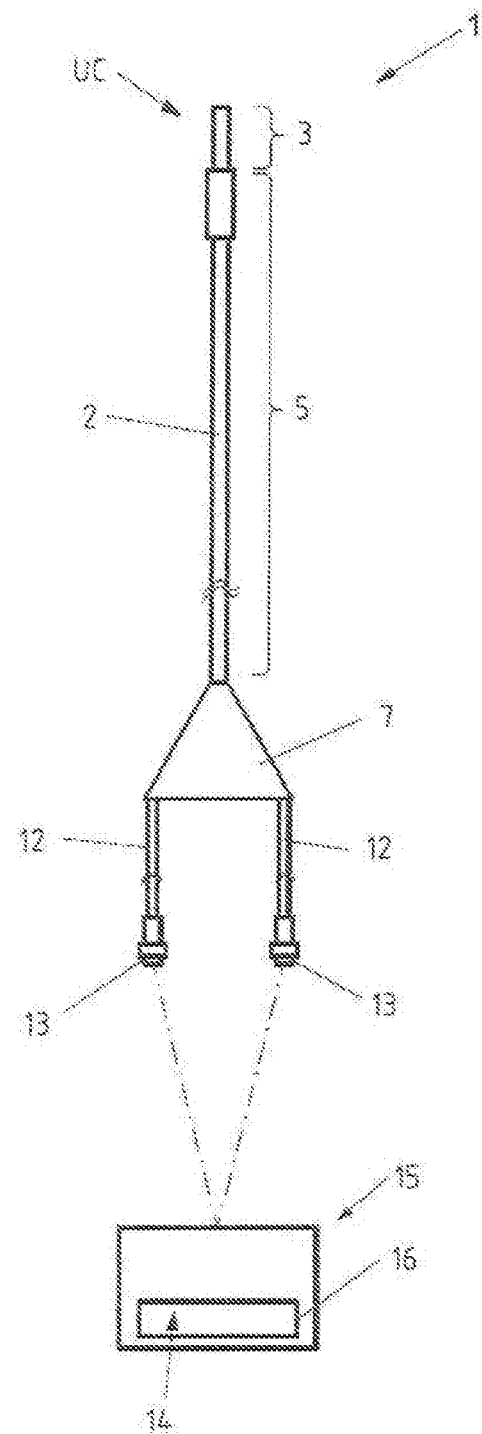
FIG. 2 is a schematic view of an electrophysiological mapping system comprising an elongated medical device for exploration or treatment of a vessel or organ or other body cavity, having an electrode assembly for electrophysiological mapping of cardiac or vessel areas, the electrode assembly being in a first, retracted condition, and a data processing and control unit/and a data output unit.
Figure 3A:
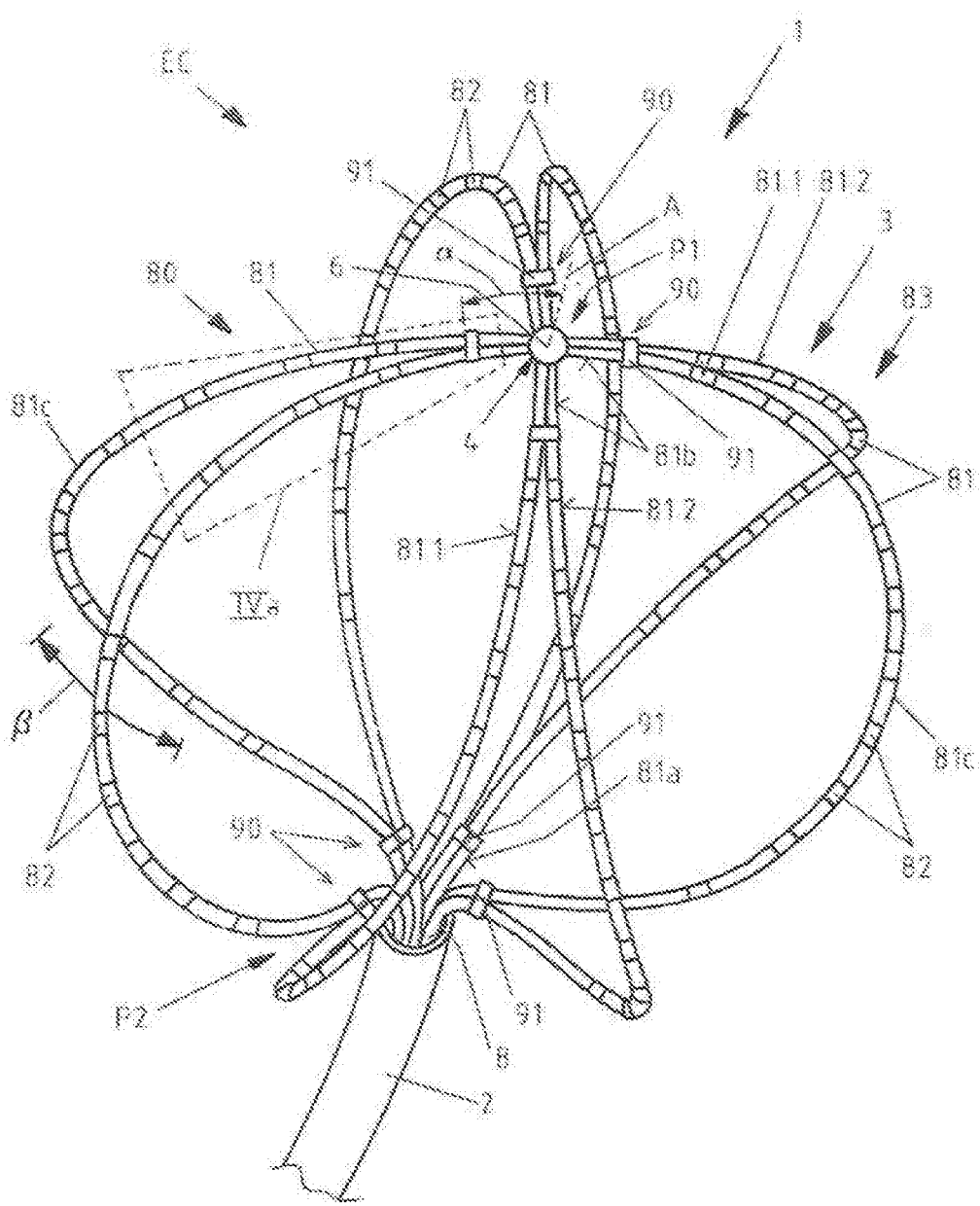
FIG. 3a is a top perspective view of a distal portion of an elongated medical device according to FIG. 2 in a second, expanded condition of the electrode assembly.

Referring to FIGS. 2, 3a, 4a and 5a, there is shown an elongated medical device 1 forming one embodiment of a mapping catheter. The elongated medical device 1 comprises an elongated body 2, comprising a distal portion 3 and a proximal portion 5. At the distal portion 3 of the elongated medical device 1, t tip 6 is arranged at the distal end 4 of the device as shown in FIG. 3a. The elongated medical device 1 further comprises an electrode assembly 80/mapping electrode assembly 80 that is located at the distal portion 3 and comprises in the embodiment of FIGS. 2 and 3a a plurality x of eight support arms 81 (or splines), where at least four (x=4) of such support arms 81 are provided. Each support arm 81 has a proximal end part 81a, a distal end part 81b and a main part 81c located between the proximal end part 81a and the distal end part 81b. The eight support arms 81 are connected to the tip 6 at their respective distal end parts 81b. Note that even and odd numbers of support arms 81 are contemplated, such as by way of non-limiting example 4, 5, 6, 7, 8, 9, 10, 11, 12, 13, 14, 15 and 16 support arms 81.

The central part 81c of each support arm 81 carries a plurality of electrodes 82 (also referred to as mapping electrodes), which according to one embodiment may comprise gold or gold plating for enhanced electro-conductivity; other suitable electrically conductive and biocompatible metals and metal alloys for the electrodes are also contemplated, such as platinum; titanium, niobium, tantalum, and/or alloys or mixtures thereof. In one embodiment ten electrodes 82 are disposed on each support arm. In some embodiments, and by way of non-limiting example, the surface area an electrode 82 may range between about 0.01 mm$^2$ and about 0.25 mm$^2$.

A basket structure electrode assembly 80 may be formed using conventional wire, braided twisted or stranded electrical conductors and conventional electrodes. Common techniques for operably connecting metal electrodes to their corresponding wire electrical conductors in medical electrical leads include welding, swaging crimping and staking. Likewise, the flexible elongated body 2 of the catheter 1 may comprise a polymeric coating or material such as silicone, polyurethane or any other suitable polymeric material. Indeed, in one embodiment catheter 1 is formed and manufactured using largely conventional manufacturing methods and materials, where lead body 2 is formed using well-known biocompatible polymeric materials that sheath or overlie internally disposed flexible electrical conductors (e.g., braided, stranded, and/or twisted wires) that are electrically connected at their distal ends to the electrodes disposed on the support arms, and the support arms themselves are formed from similar or the same biocompatible polymeric materials, flexible electrical conductors, and metal or metal alloy electrodes.

At the proximal end of the elongated medical device 1, a handle 7 or other manipulable control device may be attached to the proximal portion 5. The handle 7 may be used to manually control expansion or retraction of the electrode assembly 80 using, by way of non-limiting example, an internal pull wire operably connected to a proximal end of the support arms. When the internal pull wire is pushed in a distal direction, the support arms assume an expanded condition to form the basket structure. When the internal pull wire is pulled in a proximal direction, the support arms assume a retracted condition inside the catheter body 2.

The electrode assembly 80 in FIG. 2 is shown in its first condition UC (unexpanded condition), where the electrode assembly 80 is stored internally in space 8 within the tubular elongated body 2 of the elongated medical device 1. In this stored position the plurality of at least x=4 support arms 81 forms a dense collapsed bundle. In the first condition UC the elongated medical device 1/catheter may be introduced into a vessel, organ or other body cavity by, for example, intravascular means.

In FIG. 3a the electrode assembly 80 is in its second condition EC (expanded condition) in which the support arms 81 project away from the elongated body 2 to form a basket type structure 83, In this second expanded condition EC the device is deployed to collect electrophysiological data, i.e. for electrophysiological mapping.

As can be seen in FIG. 3a, the basket structure 83 with the support arms 81 has two pole areas P1, P2, which define a basket axis A. Between the two poles or pole areas P1, P2 each of the support arms 81 spans a curve or bow of about 180°. As shown in FIG. 3a, and in one embodiment, an angle α defines a circumferential distance along two support arms that have been combined or held together between axis A and the combining means 90 associated with the two such support arms. According to the embodiment that is employed, the angle α is not limited to circumferential distances defined by basket axis A and combining means 90, however, and can extend beyond combining means 90 or terminate prior to reaching combining means 90. In some embodiments, the circumferential distance defined by angle α delineates or approximately delineates the border or boundary between the respective proximal end parts 81a/ distal end parts 81b and the central or main parts 81c disposed along the curve or bow defined by the pertinent support arms 81. In some embodiments, the angle α ranges between about 5° and about 40°, between about 5° and about 30°, between about 5° and about 25°, between about 5° and about 20°, between about 5° and about 15°, and between about 5° and about 10°. In the embodiment of FIG. 3a, angle α is about 15°.

It should be mentioned that the number of electrodes on the support arm may be varied such that in a pair of neighboring support arms one support arm carries more electrodes than the other one. For example, one support arm may carry twelve electrodes while a neighboring support arm carries eight electrodes. With such varying numbers of electrodes, the number of electrodes in the equator area or central portion of the basket structure can be enhanced, while the number of electrodes towards the "poles" (which often produce the least useful information) may be reduced.

For example, when the electrodes 82 are disposed in the central or main part 81c of each support arm and not in the proximal end part 81 and/or the distal end part 81b of such support arm, and in the case where the angle α delineates or approximately delineates the border or boundary between such proximal end part 81a, distal end part 81b, and the central or main part 81c, electrodes 82 can be configured such that they are disposed along central or main part 81c between part 81a and distal end part 81b, and the angle α can be employed to define where electrodes are not to be found on the support arms. In such a case, the greater the angle α, the greater the circumferential distance to poles P1 or P2 from the nearest electrode 82. Such an electrode configuration can result in enhanced sensing and spatial resolution since electrodes are not being "wasted" due to their undesired proximity to the poles P1 and P2.

Figures 4A, 4B, 4C:
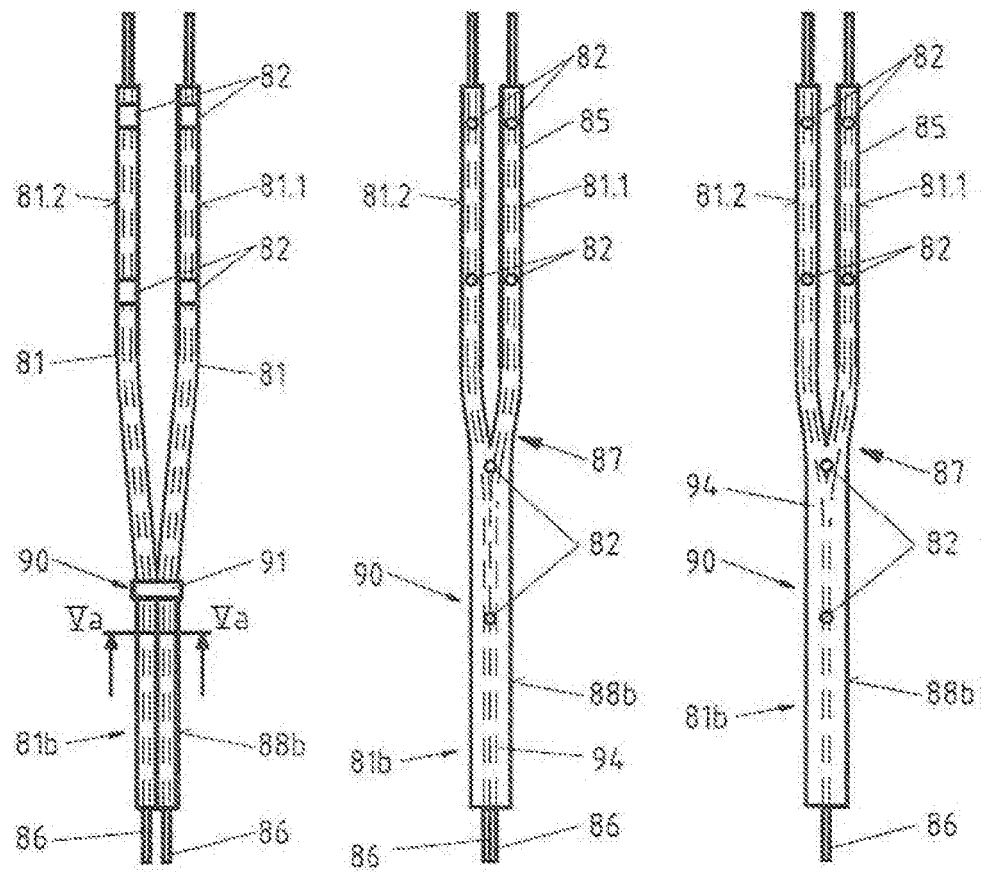
Figure 5A:
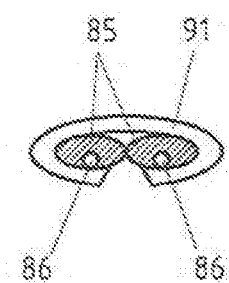

Referring to FIGS. 3a, 4a and 5a, the plurality x of eight support arms 81 is shown to comprise pairs of neighboring support arms 81.1, 81.2. In one embodiment, all first and second neighboring support arms 81.1, 81.2 are combined by combining means, member(s) and/or structure(s) 90 at their proximal end parts 81a to form united end parts 88a, so that all pairs of neighboring support arms 81.1, 81.2 are united at their proximal end parts 81a.

Further, and in some embodiments, all second and first neighboring support arms 81.2, 81.1 are combined by combining means, member(s) and/or structure(s) 90 at their distal end parts 81b to form united end parts 88b, such that all pairs of neighboring support arms 81.2, 81.1 are united at their distal end parts 81b. As shown in FIG. 3a, each support arm 81 is combined at its distal end part 81b with a neighboring support arm 81 that is different from the neighboring support arm to which it is combined or attached at its proximal end part 81a, which forms a mechanically stabilized framework that is configured to prevent or impede the undesired clustering of electrodes in only a few locations along the patient's endocardial wall or surface. Instead, the stabilized framework of support arms results in electrodes being much more evenly and regularly spaced and positioned along the patient's endocardial wall or surface during an EP mapping procedure.

Figure 6A:
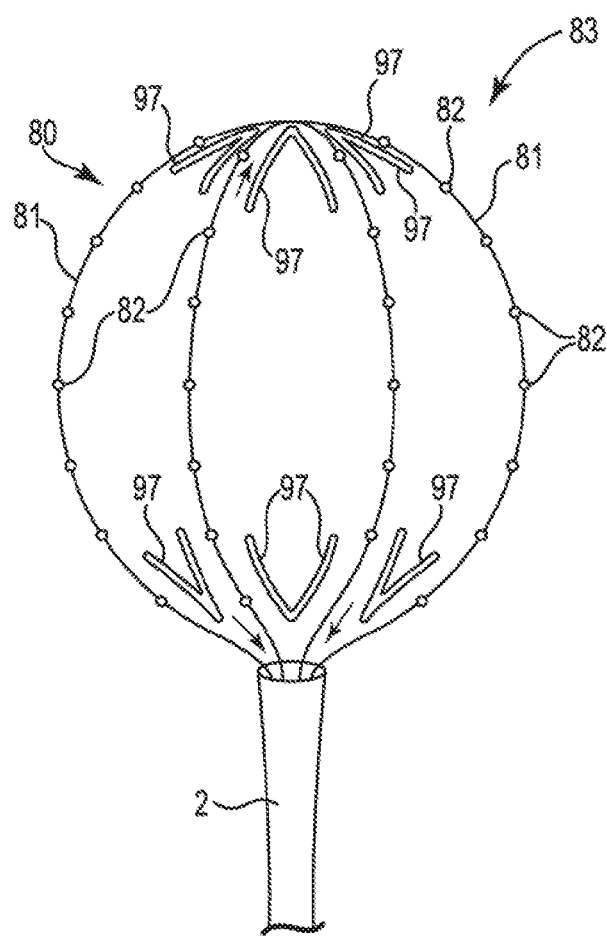
FIG. 6a shows yet another embodiment of a side perspective view of a distal portion of an elongated medical device, where the electrode assembly is shown in an expanded condition and features V- or U-shaped elements attached to adjoining support arms.
Figure 6B:
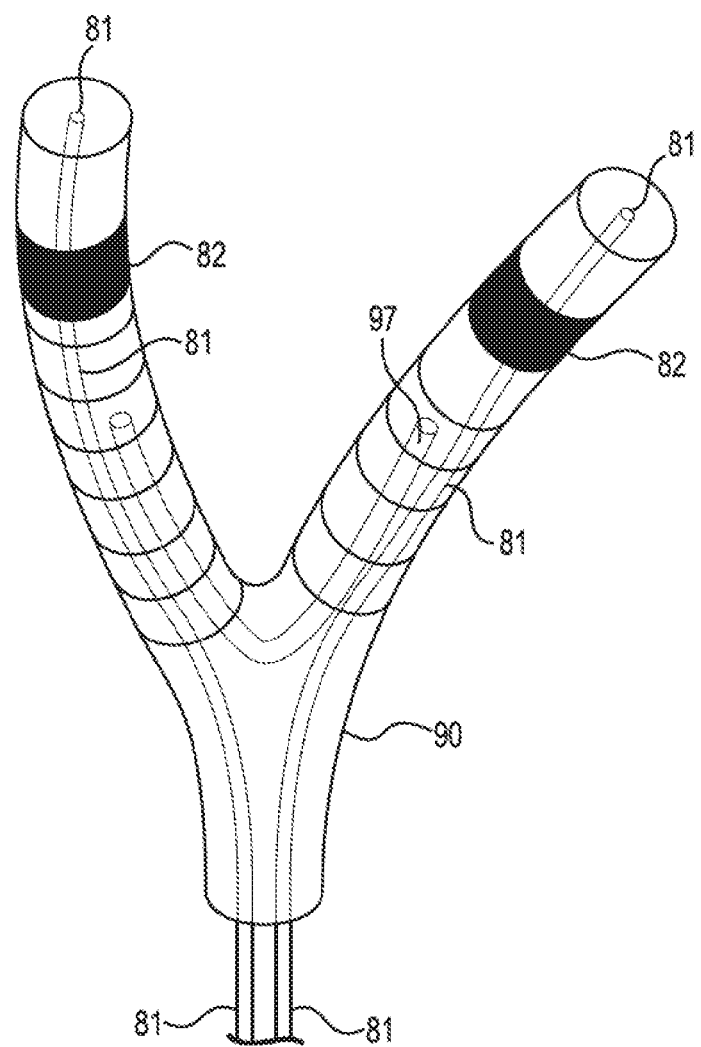
FIG. 6b shows a proximal portion of one of the support arms of FIG. 6a, and details regarding one embodiment of V- or U-shaped element and corresponding cover.

Still further, and in other embodiments, pairs of neighboring support arms 81.1 and 81.2 are combined by combining means, member(s) and/or structure(s) 90 at their distal end parts 81b to form united end parts 88b, and are also combined by combining means, member(s) and/or structure(s) 90 at their proximal end parts 81a to form united end parts 88a at their proximal end parts, such that all pairs of neighboring support arms 81.1, 81.2 are united at their distal end parts 81b and also at their proximal end parts 81a. As shown in FIGS. 6a and 6b, each support arm 81 is combined at its distal end part 81b with a neighboring support arm 81 that is the same as the neighboring support arm to which it is combined or attached at its proximal end part 81a, which also forms a mechanically stabilized framework that is configured to prevent or impede the undesired clustering of electrodes in only a few locations along the patient's endocardial wall or surface. Instead, the stabilized framework of support arms results in electrodes being much more evenly and regularly spaced and positioned along the patient's endocardial wall or surface during an EP mapping procedure.

As shown in the Figures, a modification in combining oar attaching neighboring support arms 81.1, 81.2 to one another may be employed, which besides forming united end parts 88a, 88b, further stabilizes the basket structure 83 of the electrode assembly 80. As a result, and in one embodiment, the central part 81c of an individual support arm 81 has a limited maximum angle β under which it may be deflected or bent towards a neighboring support arm when touching a surface. In one embodiment, this result is achieved at least in part by appropriate configuration of combining means, member(s) and/or structure(s) 90 with respect to the two support arms 81 to which combining means, member(s) and/or structure(s) 90 is attached. That is, combining means, member(s) and/or structure(s) 90 located at one or both ends of a given support arm 81 are configured to constrain the lateral movement of one support arm towards or in the direction of an adjoining or neighboring support arm. In one embodiment, the maximum angle β of deflection is approximately $\pm(360°/2x)$, with x being the number of support arms 81. In another embodiment, this maximum possible angle β of deflection/freedom to be bent is less than $\pm((360°/x)-(360°/10))$, with x being the number of support arms 81. Many values for angle β are contemplated, such as angle β being about 5°, about 10°, about 15°, about 20°, about 22.5°, about 25°, about 30°, and/or about 35°. Ranges of angle β are also contemplated, such as between about 5° and about 35°, between about 5° and about 30°, between about 10° and about 30°, and between about 10° and about 25°, and between about 10° and about 20°. Other ranges and values of angle β are also contemplated. As a further result, in use of the medical device, the resulting electrode distribution of the basket structure 83 when in contact with surface S is more uniform than in the prior art (where support arms tend to bunch or cluster together). In one embodiment, united end portions 88a, 88b may be formed in basket-type electrode assemblies 80 having an even number (number divisible by 2) of support arms 81.

The combining means, member(s) and/or structure(s) 90 are preferably arranged on the border between the respective proximal end parts 81a/distal end parts 81b and the central parts 81c. In case of an adhesive, welded or overmolded combining means 90, member(s) and/or structure(s), the combining means, member(s) and/or structure(s) 90 may extend between this border and the pole area along a part of the length of the neighboring proximal and/or distal end parts 81a, 81b of the support arms 81 or over the entire length of the neighboring proximal and/or distal end parts 81a, 81b.

In the embodiment of FIGS. 3a, 4a, 5a the combining means, member(s) and/or structure(s) 90 are formed as clamping elements or clamps 91. By means of the clamping elements 91 the distal end parts 81b and the proximal end parts 81a of neighboring support arms 81.1, 81.2 are clamped together in tight fit, Such clamps or clamping elements 91 may easily be applied to a basket type catheter even after the electrode assembly 80 has been mounted at the elongated medical device 1. A retrofitting of basket type catheters with combining means 90, member(s) and/or structure(s) is accordingly possible and such retrofitted catheters are also within the scope of what is described and disclosed herein.

Figure 4D:
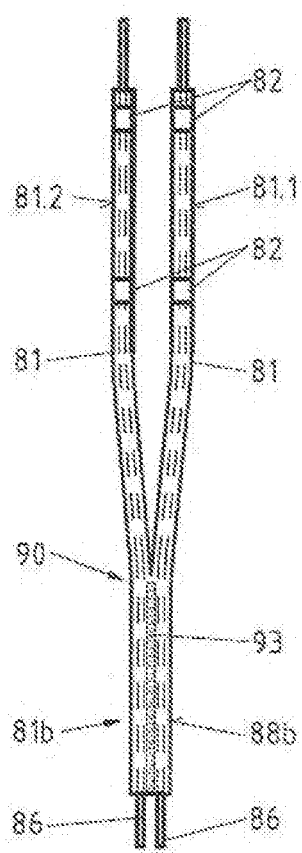
FIG. 4d is an enlarged view of an area of an electrode assembly of a further embodiment of an elongated medical device.
Figure 5B:
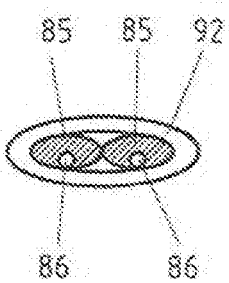
FIG. 5b is an enlarged cut section through a pair of neighboring support arms analog to FIG. 5a according to a further embodiment of an elongated medical device.

Some examples of embodiments of combining means, member(s) and/or structure(s) 91 and 92 are displayed in FIGS. 4d and 5b. Many other types of combining means, members, and/or structures are contemplated, however, including one or more of polymeric, elastomeric, adhesive, metal, metal alloy, foil, wire, woven, carbon fiber or carbon fiber layer combining means, member(s) and/or structure(s) such as, by way of non-limiting example, covers, sheaths, overmoldings, tubing(s), shrink tubing(s), clamps, ring members, rings, adhesive elements, lugs, welds, stakes, staples, crimps, polymeric, plastic metal or metal alloy stiffening members, and/or other suitable means or combining means, members and/or structures, or any combination or plurality thereof.

Figure 7:
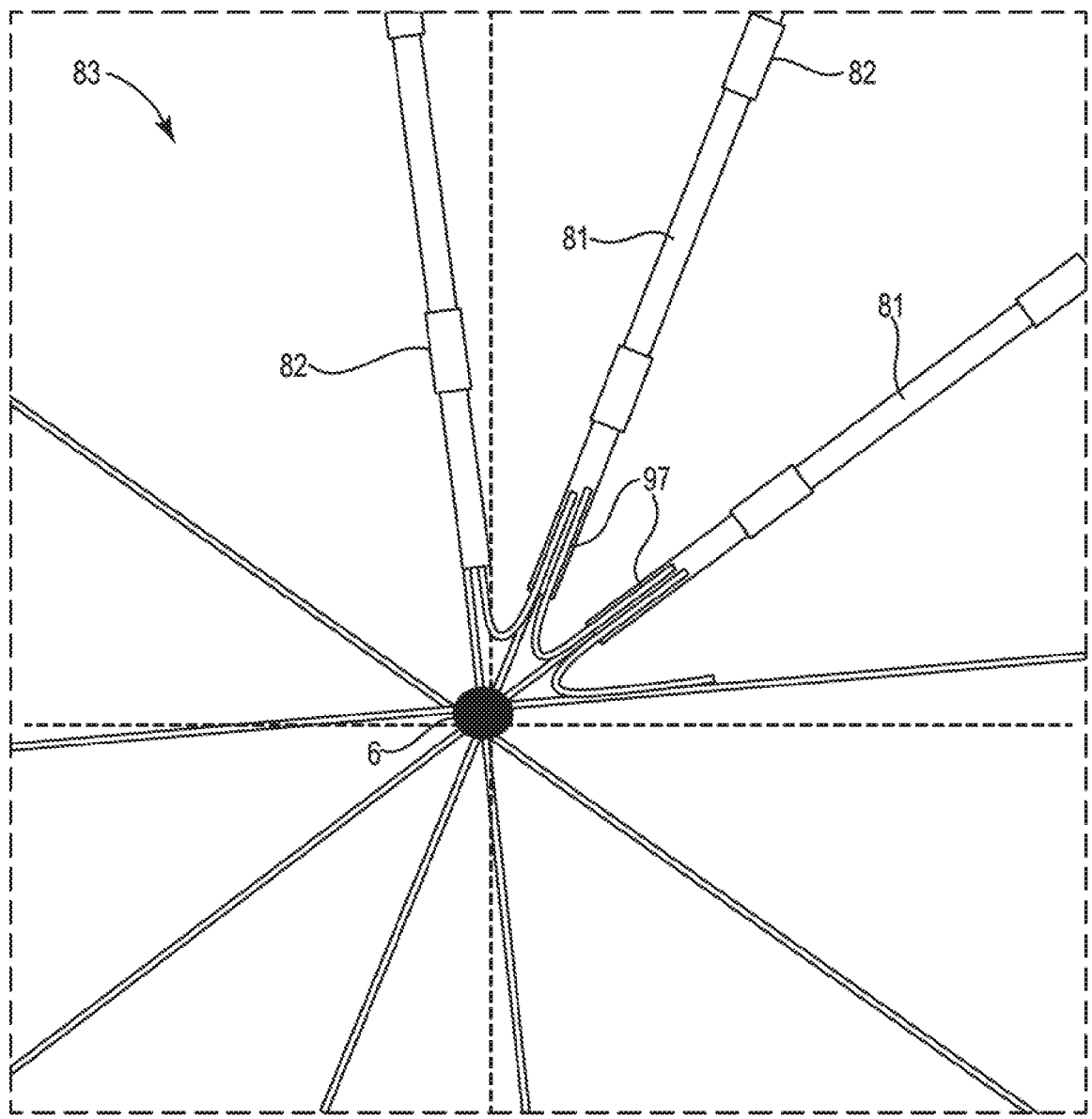
FIG. 7 shows one embodiment of an end view of a distal portion of a basket structure in a basket catheter, the basket structure comprising V- or U-shaped 7.5 elements attached to adjoining support arms.

Additionally, combining means, member(s) and/or structure(s) 90 can further comprise stiffening, directionally biased, and/or movement-, rotation- and/or twisting-limiting members 97 such as, by way of non-limiting example, V-shaped or U-shaped metal or metal alloy members, where opposing legs of a "V" or "U" are attached to adjoining but different splines. In some embodiments, the "V" or "U" corresponding to each pair of splines is oriented such that its open end points upwardly from the proximal end of the basket towards the distal end of the basket and the two legs are attached to adjoining splines, or its open end points downwardly from the distal end of the basket towards the proximal end of the basket and the two legs are attached to adjoining splines. Examples of such stiffening, directionally biased, or movement-, rotation-, and/or twisting-limiting members 97 are shown in FIGS. 6a, 6b, and 7, more about which is said below.

In the embodiment shown in FIG. 4d, the distal end parts 81b of neighboring support arms 81.1, 81.2 and the proximal end parts 81a of neighboring support arms 81.1, 81.2 are combined to form united end parts 88a, 88b by means of a joint 93 formed using an adhesive. The adhesive of joint 93 may be applied to portions or over almost the entire length of the united end parts 88a, 88b. Alternatively, a welded joint or welded connection may also be used to form joint 93.

In the embodiment shown in FIG. 5b, the distal end parts 81b of neighboring support arms 81.1, 81.2 and the proximal end parts 81a of neighboring support arms 81.1, 81.2 are combined to united end parts 88a, 88b by means of ring members or rings 92 instead of clamping elements. Clamping means of different types may also be used in combination.

Further, instead of ring member 92, a tube or shrink tube (not shown in the Figures), e.g., made of a polymeric material, may be used which may encompass or extend over the united proximal and distal end parts 81a, 81b over a part of their length or over their entire length and combine them to form the united end parts 88a, 88b.

Combining means, member(s) and/or structure(s) 90, especially in embodiments where clamps or clamping elements 91 or ring members 92 are used, may also function as mapping electrodes. The combining means, member(s) and/or structure(s) 90, formed of an electrically conductive metal, is electrically connected to electrical conductors or lines disposed in or on the support arms 81. The number of mapping electrodes may accordingly be augmented or enhanced.

Referring again to FIG. 4a, in one embodiment each of support arms 81 comprises a strand 86 formed of a shape memory metal and a PCB (printed circuit is board) layer 85, where the PCB layers 85 carry the electrodes 82 and electrical conductors (not visible in the Figures) for operative connection to electrodes 82. The PCB layers 85 at least partially surround the strands 86, which in one embodiment may be formed as Nitinol wires of 0.1-0.3 mm diameter, preferentially 0.2 mm diameter. Other suitable metals or metal alloys may also be employed to form such strands, wires or electrical conductors.

Referring again to FIGS. 2 and 3a, the electrode assembly 80 is connected via connection 12 with a data processing and control unit 15, which energizes and controls the electrodes 82. Data processing and control unit 15 processes electrode mapping data from the electrode assembly 80 and outputs mapping data on a data output screen 14 of a data output unit 16. Connection 12 may be a cable, ribbon cable, flat conductor, flat flexible cable or any other suitable electrical connection. At the end of connection or line 12 there are connectors 13 located for connecting the elongated medical device 1 and its electrode assembly 80 and associated electronics to the data processing and control unit 15.

In one embodiment, the data processing and control unit 15 may comprise a suitably programmed and configured computing device such as a personal computer. Elongated medical device 1 may form a portion of a catheter system interfaced to a computing device. In respect to the electrophysiological mapping data, in one embodiment the data processing and control unit 15 is configured to process analog and/or digitized electrode measurement data and to output data for visualizing circular excitation pattern (rotors), e.g., in the left atrium of a patient's heart on a data output screen 14 of a data output unit 16.

In operation of the medical device 1, the medical device 1 or catheter is inserted in the patient's vessel, organ or other body cavity until it reaches the target area, which in one example is the left atrium of a patient's heart, or any other portion of the heart. Upon arrival in the target area the operator may expand the electrode assembly 80 by manipulating the handle 7. In this expanded condition EC of the electrode assembly 80 and its support arms 81 the medical device 1 will be pushed with its distal end 4 against body tissue and electrophysiological mapping may be initiated automatically or by the health care provider. Data analysis of electrophysiological data, such as action potential data, is performed on the data processing and control unit 15 respectively on a suitably programmed computing device.

Figure 3B:
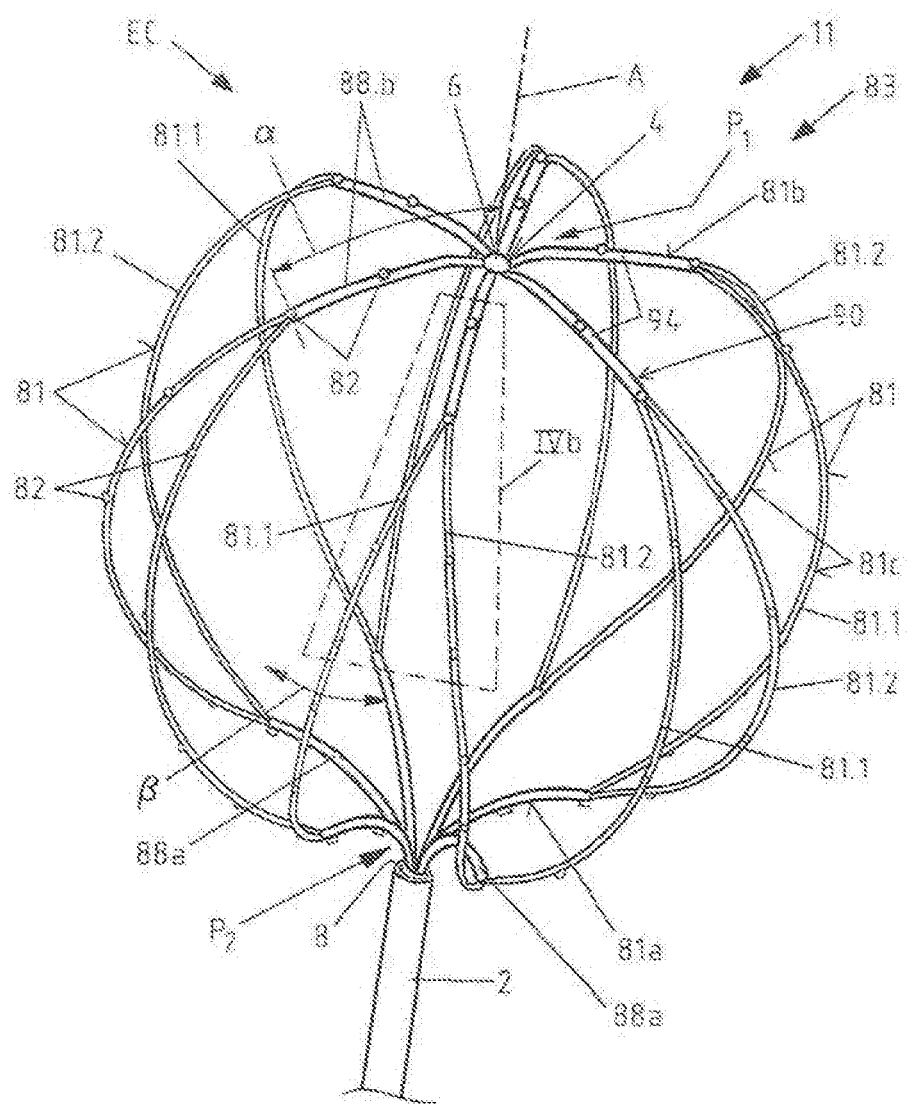
FIG. 3b is a top perspective view of a distal portion of an elongated medical device in a further embodiment in a second, expanded condition of the electrode assembly.

FIGS. 3b and 4b display a further embodiment of the elongated medical device 11. For reference numerals and functions not described in the following text, reference is made to the descriptions of FIGS. 2, 3a, 4a and 5a. Similar parts are indicated with similar reference numerals. The embodiments shown in FIGS. 3b and 4b differ from those described with respect to FIGS. 2, 3a, 4a and 5a in that the combining means, member(s) and/or structure(s) 90 in FIGS. 3b and 4b are realized in the form of a flexible electrical polymeric substrate or sheet 94 disposed at the united end parts 88a, 88b of the neighboring support arms 81.1, 81.2. Flexible electrical polymeric substrate or sheet 94 comprises electrical conductors, which in one embodiment can be made using thin film electrical conductor deposition techniques. In some embodiments, the thin film electrical conductors and their corresponding electrodes may be formed or deposited on a material chosen from the group of Mylar, Kevlar, polyimide, PEEK, an electrically conductive polyester, or other suitable flexible biocompatible materials. Flexible electrical polymeric substrate or sheet 94 may also, e.g., be formed as a PCB layer or an electro-ceramic layer. Further, and in the embodiments shown in FIGS. 3b and 4b, two electrodes 82 are disposed on each united end part 88a, 88b of the support arms 81, while four electrodes 82 are located on each central part 81c of the support arms 81.

The angle α defining the circumferential distance between the respective pole P1 or P2 and the border between the respective proximal end parts 81a/distal end parts 81b and the central parts 81c on this curve or bow is about 40° in this embodiment. Accordingly, a split point 87 (indicated in FIG. 4b) which lies in the border between the respective proximal end parts 81a/distal end parts 81b and the central parts 81c is in the same circumferential distance as defined by angle α of about 40°.

FIG. 4c displays a further embodiment of the elongated medical device similar to the embodiment of FIGS. 3b and 4b, but with modified support arms 81. For reference numerals and functions not described in the following text, reference is made to the descriptions of FIGS. 2, 3a, 3b, 4a, 4b and 5a. Similar parts are indicated with similar reference numerals. The embodiment of FIG. 4c differs from that of FIGS. 3b and 4b in that there is only one shape memory strand 86 in the united end parts 88a, 88b, whereas there are two strands 86 in the embodiment of FIGS. 3b and 4b.

At the split point 87, the single strand 86 splits into two strands 86, one in each neigh-boring support arm 81.1, 81.2. Single strand 86 may be welded in split point 87 with the two strands 86 of the neighboring support arms 81.1, 81.2.

Note that the various embodiments include those described above in the Summary, where, for example: (a) the attachment of distal and proximal end parts in neighboring support arms is reversed; (b) one end of a support arm need not be attached to a neighboring support arm (but only to a support arm that is not the same as that to which the support arm is attached or combined at another end); (c) the angle α along a support arm is constrained between certain angular limits and no electrodes are disposed on a support arm within the range of angle α; (d) the maximum angle 3 over which one support arm may be deflected towards a neighboring support arm when at least one of the arms is in contact with a surface such a patient's endocardium is constrained within certain angular limits; (e) at least some pairs of neighboring support arms are configured such that the proximal and distal ends or portions of the neighboring splines in a given pair are connected together with combining means, member(s) and/or structure(s) 90.

The various systems, devices, components and methods described and disclosed herein may also be adapted and configured for use in electrophysiological mapping applications other than those involving the interior of a patient's heart. These alternative applications include EP mapping and diagnosis of a patient's epicardium, a patient's spinal cord or other nerves, or a patient's brain or portions thereof.

In addition, the cardiac mapping catheter described and disclosed herein may be modified to include a cardiac ablation device at or near distal end 114 or tip 116. Such ablation devices may include, but are not limited to RF, cryogenic, and radioactive ablation devices. The cardiac mapping catheter may also include a force sensor, temperature sensor and/or irrigation device disposed near or at its tip 116. Moreover, the various embodiments described and disclosed herein include methods of making and using same, as described, for example, in the Summary above.

Additional embodiments can include the following elements and features:

Embodiment A

A cardiac mapping catheter configured for electrophysiological mapping and suitable for intravascular insertion in a patient's heart, comprising a flexible elongated body having a distal portion with a distal end and a proximal portion, and an electrode assembly located at the distal portion, the electrode assembly comprising a plurality x of at least 4 support arms, each support arm having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition where the plurality of support arms is arranged in a collapsed bundle, and a second expanded condition where the plurality of support arms forms an expanded basket structure, wherein the plurality of support arms further comprises first and second neighboring support arms, the proximal end parts of the first and second neighboring support arms being combined or held together near or adjoining one another, the distal end part of the first support arm being combined or held together near or adjoining a distal end part of a neighboring support arm that is not the second support arm, the distal end part of the second support arm being combined or held together near or adjoining a distal end part of a neighboring support arm that is not the first support arm, each of the plurality of support arms in the electrode assembly being combined or held together at or near its distal end part with a neighboring support arm that is different from the neighboring support arm with which it is combined or held together at its proximal end part.

Embodiment A, and other embodiments, may include one or more of the following elements or features: x is evenly divisible by the number 2; at least one of the distal end parts and the proximal end parts are combined or held together with combining means, member(s) and/or structure(s); the support arms and combining means, member(s) and/or structure(s) are together configured such that one support arm cannot be deflected or bent towards a neighboring support arm by an angle exceeding β when at least one of the arms is in contact with a surface, the angle β ranging between about 5° and about 30°; the combining means, member(s) and/or structure(s) comprises one or more of a polymeric layer, a cover, a sheath, overmolding, tubing, shrink tubing, a clamp, a ring member, an adhesive joint, a lug, a weld, a stake, a crimp, or any combination of the foregoing; at least some of the combining means, member(s) and/or structure(s) comprise an electrically conductive metal or metal alloy forming one or more electrodes, and such electrodes are electrically connected to electrical conductors disposed in one or more of the support arms; at least one of the support arms comprises a flexible electrical polymeric sheet comprising electrodes; the number x of support arms equals 4, 6, 8, 10 or 12; the number of electrodes disposed on each support arm ranges between 4 electrodes and 24 electrodes; the plurality of electrodes disposed on each support arm is distributed spatially substantially evenly thereon; the basket structure comprises two pole areas P1 and P2 that lie along a basket axis A; in the expanded condition each of the support arms spans a curve of about 180° between the two pole areas P1 and P2; an angle α defines a circumferential distance along a support arm from at least one of the poles P1 and P2 to a boundary between at least one of the proximal and distal end parts of the support arm and the central or main part of the support arm, the angle α ranges between about 5° and about 40°, and no electrodes are disposed along the circumferential distance or distances defined by the angle α; the angle α ranges between about 5° and about 30°; the angle α ranges between about 10° and about 25°; and braided, twisted or stranded electrical conductors operatively connected to the electrodes; at least portions of the flexible elongated body comprise an electrically insulative polymeric material.

Embodiment B

A method of making a cardiac mapping catheter configured for electrophysiological mapping and suitable for intravascular insertion in a patient's heart, the method comprising forming a flexible elongated body having a distal portion with a distal end and a proximal portion, and forming an electrode assembly configured to be located at or near the distal portion, the electrode assembly comprising a plurality x of at least 4 support arms, each support arm having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition where the plurality of support arms is arranged in a collapsed bundle, and a second expanded condition where the plurality of support arms forms an expanded basket structure; wherein the plurality of support arms further comprises first and second neighboring support arms, the proximal end parts of the first and second neighboring support arms being combined or held together near or adjoining one another, the distal end part of the first support arm being combined or held together near or adjoining a distal end part of a neighboring support arm that is not the second support arm, the distal end part of the second support arm being combined or held together near or adjoining a distal end part of a neighboring support arm that is not the first support arm, each of the plurality of support arms in the electrode assembly being combined or held together at or near its distal end part with a neighboring support arm that is different from the neighboring support arm with which it is combined or held together at its proximal end part.

Embodiment B, and other embodiments, may include one or more of the following elements, features or steps: x is evenly divisible by the number 2; combining or holding together the distal end parts or proximal end parts with combining means, member(s) and/or structure(s); one or more of a polymeric layer, a cover, a sheath; overmolding, tubing; shrink tubing, a clamp, a ring member, an adhesive joint, a lug, a weld, a stake, a crimp, or any combination of the foregoing; the support arms are formed using a flexible electrical polymeric sheet; an angle α defines a circumferential distance along a support arm from at least one of the poles P1 and P2 to a boundary between at least one of the proximal and distal end parts of the support arm and the central or main part of the support arm, the angle α ranges between about 5° and about 40°, and no electrodes are disposed along the circumferential distance or distances defined by the angle α; the angle α ranges between about 5° and about 30°; the angle α ranges between about 10° and about 25°; operatively connecting braided, twisted or stranded electrical conductors to the electrodes; and forming at least portions of the flexible elongated body with an electrically insulative polymeric material.

Embodiment C

A cardiac mapping catheter configured for electrophysiological mapping and suitable for intravascular insertion in a patient's heart, comprising a flexible elongated body having a distal portion with a distal end and a proximal portion, and an electrode assembly located at the distal portion, the electrode assembly comprising a plurality x of at least 4 support arms, each support arm having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition where the plurality of support arms is arranged in a collapsed bundle, and a second expanded condition where the plurality of support arms forms an expanded basket structure, wherein the plurality of support arms further comprises first and second neighboring support arms, the distal end parts of the first and second neighboring support arms being combined or held together near or adjoining one another, the proximal end part of the first support arm being combined or held together near or adjoining a proximal end part of a neighboring support arm that is not the second support arm, the proximal end part of the second support arm being combined or held together near or adjoining a proximal end part of a neighboring support arm that is not the first support arm, each of the plurality of support arms in the electrode assembly being combined or held together at or near its proximal end part with a neighboring support arm that is different from the neighboring support arm with which it is combined or held together at its distal end part.

Embodiment C, and other embodiments, may include one or more of the following elements or features: x is evenly divisible by the number 2.

Embodiment D

A cardiac mapping catheter configured for electrophysiological mapping and suitable for intravascular insertion in a patient's heart, comprising a flexible elongated body having a distal portion with a distal end and a proximal portion, and an electrode assembly located at the distal portion, the electrode assembly comprising a plurality x of at least 4 support arms, each support arm having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition where the plurality of support arms is arranged in a collapsed bundle, and a second expanded condition where the plurality of support arms forms an expanded basket structure; wherein the basket structure comprises two pole areas P1 and P2 that lie along a basket axis A, in the expanded condition each of the support arms spans a curve of about 180° between the two pole areas P1 and P2, an angle $\alpha$ defines a circumferential distance along a support arm from at least one of the poles P1 and P2 to a boundary between at least one of the proximal and distal end parts of the support arm and the central or main part of the support arm, the angle $\alpha$ ranges between about 5° and about 40°, and no electrodes are disposed along the circumferential distance or distances defined by the angle $\alpha$.

Embodiment E

A cardiac mapping catheter configured for electrophysiological mapping and suitable for intravascular insertion in a patient's heart, comprising a flexible elongated body having a distal portion with a distal end and a proximal portion, and an electrode assembly located at the distal portion, the electrode assembly comprising a plurality x of at least 4 support arms, each support arm having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition where the plurality of support arms is arranged in a collapsed bundle, and a second expanded condition where the plurality of support arms forms an expanded basket structure; wherein the proximal end part of each support arm is combined or held near or together with the proximal end part of a neighboring support arm, and the distal end part of each support member is combined or held near or together with the distal end part of a support arm that is not the neighboring support arm.

Embodiment F

A cardiac mapping catheter configured for electrophysiological mapping and suitable for intravascular insertion in a patient's heart, comprising a flexible elongated body having a distal portion with a distal end and a proximal portion, and an electrode assembly located at the distal portion, the electrode assembly comprising a plurality x of at least 4 support arms, each support arm having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition where the plurality of support arms is arranged in a collapsed bundle, and a second expanded condition where the plurality of support arms forms an expanded basket structure; wherein the distal end part of each support arm is combined or held near or together with the distal end part of a neighboring support arm, and the proximal end part of each support member is combined or held near or together with the proximal end part of a support arm that is not the neighboring support arm.

Embodiment G

A cardiac mapping catheter configured for electrophysiological mapping and suitable for intravascular insertion in a patient's heart, comprising a flexible elongated body having a distal portion with a distal end and a proximal portion, and an electrode assembly located at the distal portion, the electrode assembly comprising a plurality x of at least 4 support arms, each support arm having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition where the plurality of support arms is arranged in a collapsed bundle, and a second expanded condition where the plurality of support arms forms an expanded basket structure, at least one of the distal end parts and the proximal end parts being combined or held together with combining means, member(s) and/or structure(s), wherein the support arms and combining means, member(s) and/or structure(s) are together configured such that one support arm may be not be deflected or bent towards a neighboring support arm by an angle exceeding $\beta$ when at least one of the arms is in contact with a surface, the angle 3 ranging between about 5° and about 30°.

Embodiment H

A cardiac mapping catheter configured for electrophysiological mapping and suitable for intravascular insertion in a patient's heart, comprising a flexible elongated body having a distal portion with a distal end and a proximal portion, and an electrode assembly located at the distal portion, the electrode assembly comprising a plurality x of at least 4 support arms, each support arm having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition where the plurality of support arms is arranged in a collapsed bundle, and a second expanded condition where the plurality of support arms forms an expanded basket structure, at least one of the distal end parts and the proximal end parts being combined or held together with combining means, member(s) and/or structure(s), wherein the distal end part of each support arm is combined or held near or together with the distal end part of a neighboring support arm, and the proximal end part of each support member is combined or held near or together with the proximal end part of the same adjoining neighboring support arm.

Embodiment I

A cardiac mapping catheter configured for electrophysiological mapping and suitable for intravascular insertion in a patient's heart, the catheter comprising a flexible elongated body having a distal portion with a distal end and a proximal portion, and an electrode assembly located at the distal portion, the electrode assembly comprising a plurality of support arms, each support arm having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition, where the plurality of support arms is arranged in a collapsed bundle, and a second expanded condition, where the plurality of support arms forms an expanded basket structure, at least one of two or more neighboring distal end parts and two or more neighboring proximal end parts being combined, attached to one another, or held together with one or more combining means, members or structures, and further wherein the combining means, members or structures further are configured to act as or comprise at least one of stiffening, directionally biased, movement-limiting, rotation-limiting, and twisting-limiting means, members or structures, such stiffening means, members or structures being configured to prevent bunching and promote spacing apart of adjoining support arms when the expanded basket structure is deployed inside a patient's heart in the expanded second condition.

Embodiment J

A method of making a cardiac mapping catheter configured for electrophysiological mapping and suitable for intravascular insertion in a patient's heart, the method comprising forming a flexible elongated body having a distal portion with a distal end and a proximal portion, and forming an electrode assembly located at the distal portion, the electrode assembly comprising a plurality of support arms, each support arm having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition, where the plurality of support arms is arranged in a collapsed bundle, and a second expanded condition, where the plurality of support arms forms an expanded basket structure, at least one of two or more neighboring distal end parts and two or more neighboring proximal end parts being combined, attached to one another, or held together with one or more combining means, members or structures, wherein the combining means, members or structures further are configured to act as or comprise at least one of stiffening, directionally biased, movement-limiting, rotation-limiting, and twisting-limiting means, members or structures, such stiffening means, members or structures being configured to prevent bunching and promote spacing apart of adjoining support arms when the plurality of support arms and the expanded basket structure is deployed inside a patient's heart in the expanded second condition.

Embodiment K

A cardiac mapping catheter configured for electrophysiological mapping and suitable for intravascular insertion in a patient's heart, the catheter comprising a flexible elongated body having a distal portion with a distal end and a proximal portion, and an electrode assembly located at the distal portion, the electrode assembly comprising a plurality of support arms comprising Nitinol or shape memory alloy splines, each spline having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition, where the plurality of support arms is arranged in a collapsed bundle, and a second expanded condition, where the plurality of support arms forms an expanded basket structure, wherein the Nitinol splines are cut from a single sheet of Nitinol or shape memory alloy disposed or located on a flat or substantially flat surface during cutting, each spline being cut from the sheet such that at its proximal end part each spline terminates in a collar contiguous with the proximal end part of the spline, the collar being cut from the same sheet of Nitinol or shape memory alloy as the spline, wherein each spline is cut from the flat or substantially flat sheet such that between its proximal end part and its distal end part each spline forms a series of compound curves or arcs that curve first in a first general direction and then curve second in a second general direction opposite or partially opposite to or from the first direction, the distal end parts of the splines forming separate distal ends that are not connected to one another, the splines being nested together on the flat or substantially flat surface when the curves in the splines are being cut such that the splines are adjacent to one another and are separated from adjoining splines by continuous intervening spaces formed between the proximal end parts and the distal ends of the splines during cutting, the collar being configured, after cutting, to be joined, attached, or secured to the distal portion or distal end of the elongated body or to a distal tip of the basket structure, and further wherein after the splines have been formed from the sheet, after the collar has been attached to the distal portion or distal end of the elongated body, and after the distal ends of the splines have been attached or secured to the distal tip, the basket structure forms a series of spirally winding or spirally wrapping support arms when deployed in the second expanded condition, the basket structure and electrodes being configured to prevent bunching and promote spacing apart of adjoining support arms when the expanded basket structure is deployed inside a patient's heart in the expanded second condition.

Embodiment L

A method of making a cardiac mapping catheter configured for electrophysiological mapping and suitable for intravascular insertion in a patient's heart, the catheter comprising a flexible elongated body having a distal portion with a distal end and a proximal portion, and an electrode assembly located at the distal portion, the electrode assembly comprising a plurality of support arms comprising Nitinol or shape memory alloy splines, each spline having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition, where the plurality of support arms is arranged in a collapsed bundle, and a second expanded condition, where the plurality of support arms forms an expanded basket structure, the method comprising cutting the Nitinol splines from a single sheet of Nitinol or shape memory alloy disposed or located on a flat or substantially flat surface during cutting, cutting each spline from the sheet such that at its proximal end part each spline terminates in a collar contiguous with the proximal end part of the spline, cutting the collar from the same sheet of Nitinol or shape memory alloy as the spline, cutting each spline from the flat or substantially flat sheet such that between its proximal end part and its distal end part each spline forms a series of compound curves or arcs that curve first in a first general direction and then curve second in a second general direction opposite or partially opposite to or from the first direction, the distal end parts of the splines forming separate distal ends that are not connected to one another, the splines being nested together on the flat or substantially flat surface while the curves in the splines are being cut such that the splines are adjacent to one another and are separated from adjoining splines by continuous intervening spaces formed between the proximal end parts and the distal ends of the splines during cutting, and configuring the collar, after cutting, to be joined, attached, or secured to the distal portion or distal end of the elongated body or to a distal tip of the basket structure, wherein after the splines have been formed from the sheet, after the collar has been attached to the distal portion or distal end of the elongated body, and after the distal ends of the splines have been attached or secured to the distal tip, the basket structure forms a series of spirally winding or spirally wrapping support arms when deployed in the second expanded condition, the basket structure and electrodes being configured to prevent bunching and promote spacing apart of adjoining support arms when the expanded basket structure is deployed inside a patient's heart in the expanded second condition.

Embodiment M

A cardiac mapping catheter configured for electrophysiological mapping and suitable for intravascular insertion in a patient's heart, the catheter comprising a flexible elongated body having a distal portion with a distal end and a proximal portion, and an electrode assembly located at the distal portion, the electrode assembly comprising a plurality of support arms comprising Nitinol or shape memory alloy splines, each spline having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition, where the plurality of support arms is arranged in a collapsed bundle, and a second expanded condition, where the plurality of support arms forms an expanded basket structure, wherein the Nitinol or shape memory alloy splines are cut from a single tube of Nitinol or shape memory alloy, each spline being formed or cut from the tube such that at its distal end part each spline terminates in a ring or collar contiguous with the distal end part of the spline, the ring or collar being cut from the same tube of Nitinol or shape memory alloy as the splines and forming a distal portion of the basket structure, the proximal end parts of the splines forming separate proximal ends that are not connected to one another after being cut from the tube, the proximal ends of the splines being configured, after cutting, to be joined, attached, or secured to the distal portion or distal end of the elongated body, and further wherein after the splines have been formed from the tube, and after the proximal ends of the splines have been attached or secured to the distal portion or the distal end part of the flexible elongated body, the basket structure comprises a plurality of outwardly bowing or curved splines when deployed in the second expanded condition.

Embodiment N

A method of making a cardiac mapping catheter configured for electrophysiological mapping and suitable for intravascular insertion in a patient's heart, the catheter comprising a flexible elongated body having a distal portion with a distal end and a proximal portion, and an electrode assembly located at the distal portion, the electrode assembly comprising a plurality of support arms comprising Nitinol or shape memory alloy splines, each spline having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition, where the plurality of support arms is arranged in a collapsed bundle, and a second expanded condition, where the plurality of support arms forms an expanded basket structure, the method comprising cutting the Nitinol splines from a single tube of Nitinol or shape memory alloy; cutting each spline from the tube such that at its distal end part each spline terminates in a collar or ring contiguous with the distal end part of the spline, the collar or ring being cut from the same tube of Nitinol or shape memory alloy as the splines; further cutting each spline from the tube such the proximal end parts of each spline not connected to one another, and joining, attaching, or securing the proximal end parts of the splines to the distal portion or distal end of the elongated body; wherein after the splines have been formed from the tube, after the proximal end parts of the splines have been joined, attached, or secured to the distal portion or distal end of the elongated body, the basket structure comprises a plurality of outwardly bowing or curved splines when deployed in the second expanded condition.

In still other embodiments, conventional basket electrode splines comprising, by way of non-limiting example, electrical conductors operably connected to the electrodes mounted or attached thereto, electrically insulative material or coatings separating the individual electrical conductors, and an optional shape memory alloy, metal, and/or metal alloy member, layer, or wire disposed along or in each spline, are employed in basket type structure 83 in combination with any of the various combining means, member(s) and/or structure(s) discussed herein.

In still further embodiments, one or more pairs of support arms that are connected by combining means, members and/or structures at both of their corresponding distal and proximal end parts can be combined in a basket catheter with one more support arms that have at least one of their distal or proximal end parts attached by combining means, member(s) and/or structure(s) to a neighboring support arm that is not the same support arm to which the opposing end of the support arm is connected by another combining means, member(s) or structure(s).

Referring now to FIGS. 6*a*, 6*b* and 7, there are shown some non-limiting embodiments of a basket structure 83 in an elongated medical device 1, where at least one of two or more neighboring distal end parts and two or more neighboring proximal end parts of support arms 81 are combined, attached to one another, or held together with one or more combining means, members or structures 90, 91, and/or 97, and wherein the combining means, members or structures further are configured to act as or comprise at least one of stiffening, directionally biased, movement-limiting, rotation-limiting, and twisting-limiting means, members or structures 97. Such stiffening means, members or structures are configured to prevent bunching and promote spacing apart of adjoining support arms 81 when the expanded basket structure 83 is deployed inside a patient's heart in the expanded second condition. Note that according to various embodiments, the combining means, members, or structures 90 or 91 can be the same as or separate from stiffening means, members, or structures 97. Those skilled in the art will understand after having read and understood the present disclosure and drawings that many different permutations, combinations and modifications of combining means, members or structures 90, 91, and/or 97, and of stiffening, directionally biased, movement-limiting, rotation-limiting, and twisting-limiting means, members or structures 97, are contemplated and possible.

Continuing to refer to FIGS. 6*a*, 6*b* and 7, stiffening, directionally biased, movement-limiting, rotation-limiting, and twisting-limiting means, members or structures 97 comprise one or more of V- or U-shaped elements, such as the V- or U-shaped elements forming opposing legs attached to adjoining but different support arms 81 of basket structure 83 shown in FIGS. 6*a* and 6*b*. V- or U-shaped elements 97 may also correspond to at least one of pairs of elements 97 oriented such that their open ends point upwardly from the proximal end of the basket structure 83 towards the distal end of the basket structure 83, and pairs of elements 97 oriented such that their open ends point downwardly from the distal end of the basket structure towards the proximal end of the basket structure, as shown in FIG. 6*a*.

In other embodiments, at least one of the distal end parts and the proximal end parts of at least some supporting members 81 are not combined or held together with combining means, members or structures 90 or by stiffening, directionally biased, movement-limiting, rotation-limiting, and twisting-limiting means, members or structures 97. In some embodiments, at least one of the support arms 81 and combining means 90 and/or stiffening, directionally biased, movement-limiting, rotation-limiting, and twisting-limiting means, members or structures 97 are together configured such that one support arm 81 cannot be deflected or bent towards a neighboring support arm 81 by an angle exceeding β when the at least one support arms is in contact with a surface (e.g., a patient's atrial wall), the angle β ranging between about 5° and about 30°.

In still other embodiments, at least one of the combining means, members or structures and the stiffening means, members or structures comprise one or more of clamping elements, clamps, polymeric, elastomeric, adhesive, metal, metal alloy, foil, wire, woven, carbon fiber or carbon fiber layer combining or stiffening means, members r structures, covers, sheaths, overmoldings, tubing, shrink tubing, ring members, rings, adhesive elements, lugs, welds, stakes, staples, crimps, polymeric, plastic metal, or metal alloy stiffening members, or any combination of the foregoing.

In still further embodiments, at least one of the support arms 81 comprises a Nitinol spline having electrodes mounted thereon or attached thereto, or at least one of the support arms 81 comprises a flexible electrical polymeric sheet or flex circuit comprising electrodes and associated circuitry. In some embodiments, the number of support arms 81 equals 4, 6, 8, 10 or 12. Other numbers of support arms 81 are also contemplated. By way of non-limiting example, the number of electrodes 82 disposed on each support arm 81 may range between 4 electrodes and 24 electrodes, and the plurality of electrodes disposed on each support arm 81 may be distributed spatially substantially evenly thereon.

FIG. 6*b* shows an illustrative but non-limiting example and embodiment of a proximal portion of one of the support arms 81 in FIG. 6*a*. As shown, stiffening member 97 is V- or U-shaped, and points upwardly towards the distal end of basket structure 83. The illustrated Nitinol splines 81 are encased by plastic or polymeric cover 90, which can be configured to cover major or minor portions of spline or support arm 81, and around or into which electrodes 82 can be formed or located.

FIG. 7 shows one embodiment of an end view of the distal end of basket structure 83, with distal cap 6 having attached or connected thereto the distal ends of splines or support arms 81. Corresponding stiffening means, elements or structures 97 are disposed between and attached to some or all neighboring pairs of splines or support arms 81.

Further contemplated herein are the various methods of making a cardiac mapping catheter configured for electrophysiological mapping and suitable for intravascular insertion in a patient's heart. In some embodiments, such methods comprise: (a) forming a flexible elongated body having a distal portion with a distal end and a proximal portion, and (b) forming an electrode assembly located at the distal portion, the electrode assembly comprising a plurality of support arms, each support arm having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition, where the plurality of support arms is arranged in a collapsed bundle, and a second expanded condition, where the plurality of support arms forms an expanded basket structure, at least one of two or more neighboring distal end parts and two or more neighboring proximal end parts being combined, attached to one another, or held together with one or more combining means, members or structures, and wherein the combining means, members or structures further are configured to act as or comprise at least one of stiffening, directionally biased, movement-limiting, rotation-limiting, and twisting-limiting means, members or structures, such stiffening means, members or structures being configured to prevent bunching and promote spacing apart of adjoining support arms when the plurality of support arms and the expanded basket structure is deployed inside a patient's heart in the expanded second condition. Such methods can further comprise forming at least one of the combining means, members or structures and the stiffening means, members or structures from one or more of clamping elements, clamps, polymeric, elastomeric, adhesive, metal, metal alloy, foil, wire, woven, carbon fiber or carbon fiber layer combining or stiffening means, members r structures, covers, sheaths, overmoldings, tubing, shrink tubing, ring members, rings, adhesive elements, lugs, welds, stakes, staples, crimps, polymeric, plastic metal, or metal alloy stiffening members, or any combination of the foregoing.

Figure 8:
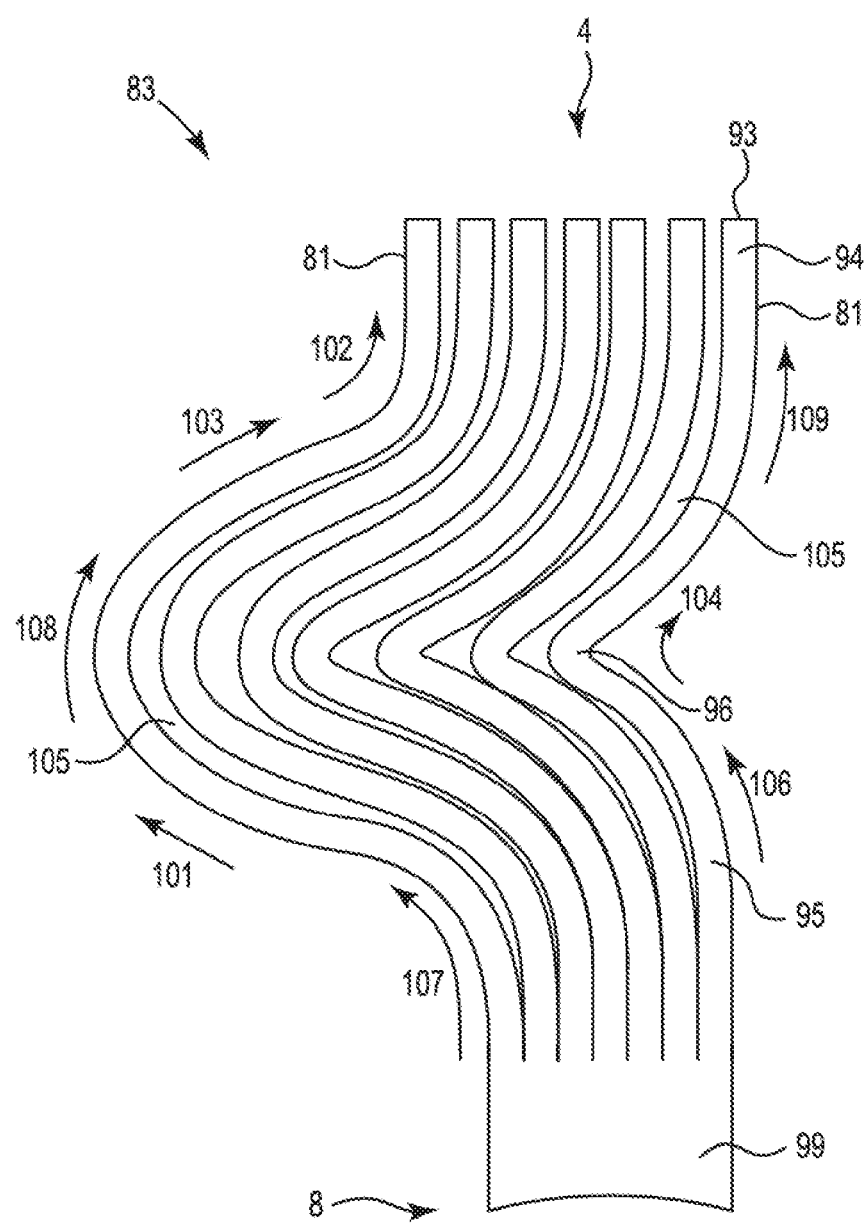
FIG. 8 shows one embodiment of Nitinol splines cut from a sheet of Nitinol metal, where the splines are configured and shaped for use in a basket structure of a basket catheter.
Figure 9:
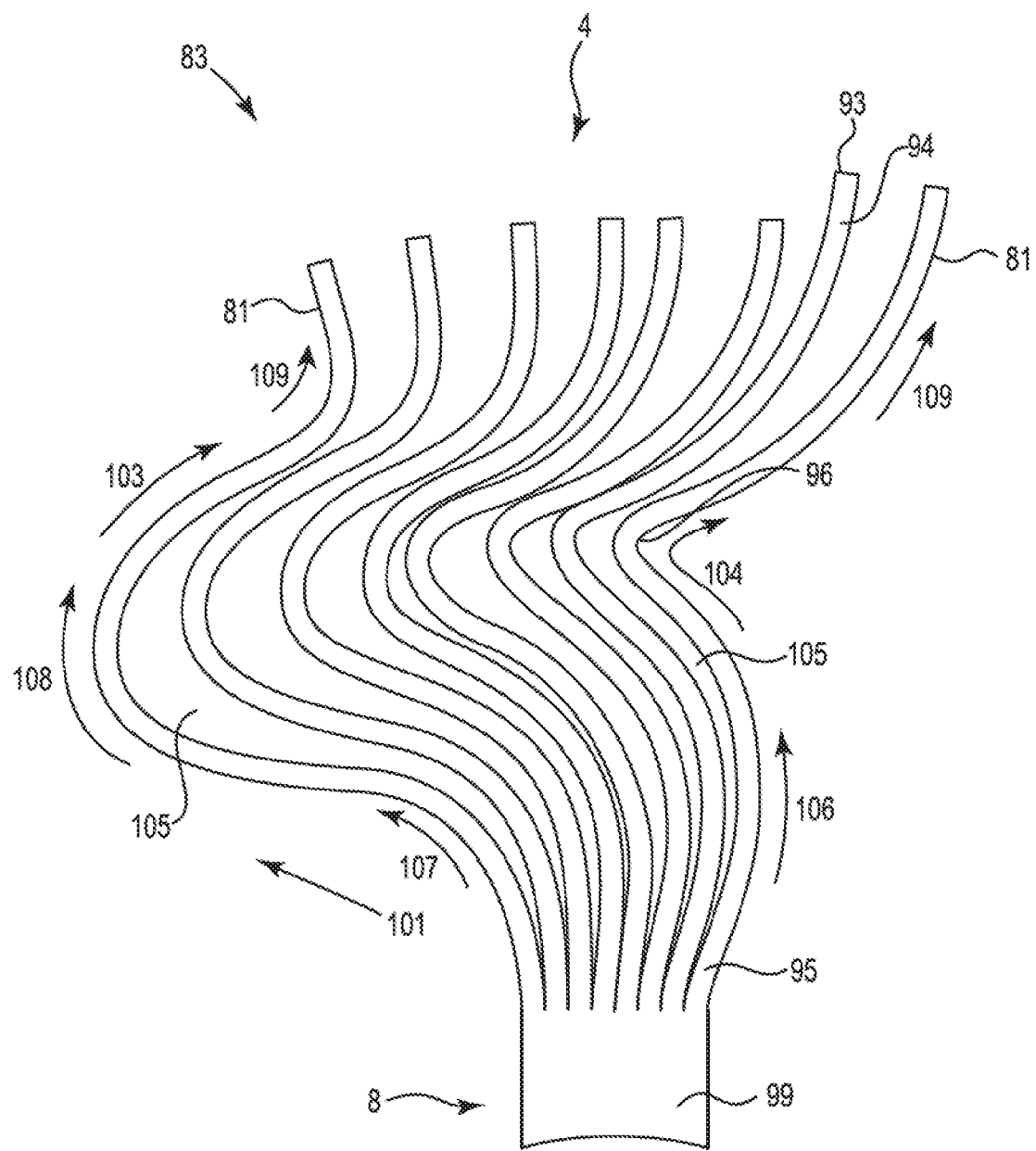
FIG. 9 shows the embodiment of Nitinol splines cut from a sheet of Nitinol metal of FIG. 8, where the splines 81 are spatially separated from one another.
Figure 10A:
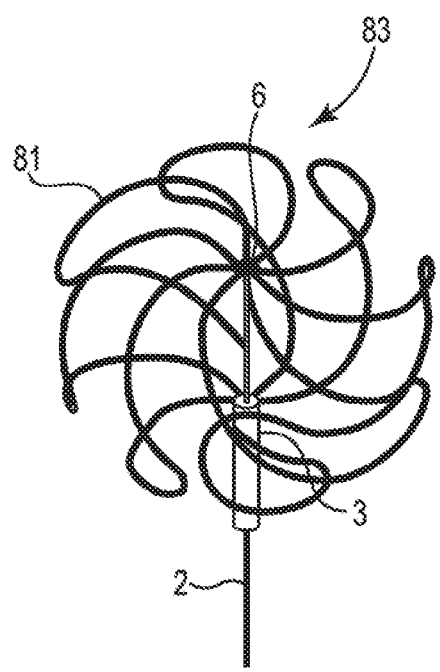
FIGS. 10a and 10b show side and top perspective views, respectively, of the Nitinol basket structure of FIGS. 8 and 9 in expanded and deployed configurations, where the proximal portion of basket structure has been operably attached to a proximally located elongated catheter body.
Figure 10B:
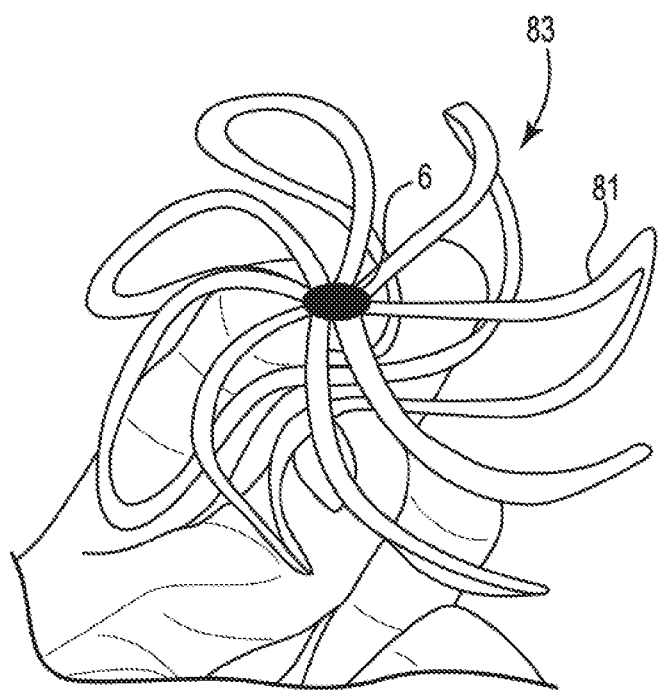

FIG. 8 shows one embodiment of Nitinol splines 81 cut from a single sheet of Nitinol metal, where the splines 81 are configured and shaped for use in a basket structure of a basket catheter. FIG. 9 shows the embodiment of Nitinol splines cut from a single sheet of Nitinol metal of FIG. 8, where the splines 81 are shown spatially separated from one another. FIGS. 10a and 10b show side and top perspective views, respectively, of the Nitinol basket structure of FIGS. 8 and 9 in expanded and deployed configurations, where the proximal portion of basket structure forming a collar 99 has been operably attached to a proximally located portion of elongated catheter body 2.

Continuing to refer to FIGS. 8 through 10b, an electrode assembly 80 comprises a plurality of support arms 81 comprising Nitinol or shape memory alloy splines, each spline having a proximal end part 95, a distal end 93, a distal end part 94, and a main part 96 located between the proximal end part 95 and the distal end part 94. Each of the plurality of support arms 81 comprises a plurality of electrodes 82 (not shown in FIGS. 8 and 19, but shown in FIGS. 10a and 10b). The electrodes 82 are configured to acquire electrophysiological signals from the patient's heart.

The plurality of support arms 81 is configured to have a first retracted condition, where the plurality of support arms 81 is arranged in a collapsed bundle, and a second expanded condition, where the plurality of support arms 81 forms an expanded basket structure 83. The Nitinol splines forming support arms 81 are cut from a single sheet of Nitinol or shape memory alloy disposed or located on a flat or substantially flat surface during cutting.

Each spline 81 is cut from the sheet such that at its proximal end part 95 each spline 81 terminates in a collar 99 that is contiguous with the proximal end part 95 of the spline 81. The collar 99 is cut from the same sheet of Nitinol or shape memory alloy as the spline 81. The collar 99 is configured, after cutting, to be joined, attached, or secured to the distal portion or distal end 3 of the elongated body 2, or in an alternative embodiment to a distal tip 6 of the basket structure 83.

Each spline is cut from the flat or substantially flat sheet such that between its proximal end part 95 and its distal end part 94 each spline 81 forms a series of compound curves or arcs that curve first in a first general direction 101 and then curve second in a second general direction 103 opposite or partially opposite to or from the first direction 101. The distal end parts 94 of the splines 81 form separate distal ends 93 that are not connected to one another, and the splines 81 are nested together on the flat or substantially flat surface when the curves in the splines 81 are being cut such that the splines 81 are adjacent to one another and are separated from adjoining 81 splines by continuous intervening spaces 105 formed between the proximal end parts 95 and the distal end parts 94 of the splines 81 during cutting. After the splines 81 have been formed from the sheet, after the collar 99 has been attached to the distal portion or distal end 3 of the elongated body 2, and after the distal ends 93 of the splines 81 have been attached or secured to the distal tip 6, the basket structure 83 forms a series of spirally winding or spirally wrapping support arms 81 when deployed in the second expanded condition. The basket structure 83 and electrodes 82 are configured to prevent bunching and promote spacing apart of adjoining support arms when the expanded basket structure 83 is deployed inside a patient's heart in the expanded second condition (see FIGS. 10a and 10b).

In the embodiments shown in FIGS. 10a and 10b, it will be seen that the resulting basket structure 83 is configured to more evenly distribute electrodes 82 over the inner walls of a patient's atrium than in some conventional basket structure designs, which employ linear or straight splines more prone to bunching and uneven electrode distribution within a patient's atrium. Note that the spirally wound or winding spline configurations shown in FIGS. 10a and 10b may also be employed when cutting or forming splines 81 from a single tube, as discussed in detail below (i.e., cuts or slits 105 shown in FIG. 11 may be curved instead of straight).

Continuing to refer to FIGS. 8 through 10b, and also to FIGS. 11 and 12 (more about which is said below), note that combining means, member(s) and/or structure(s) 90 and/or stiffening, directionally biased, and/or movement-, rotation- and/or twisting-limiting members 97 described above may also be employed in conjunction with the Nitinol basket structures 83 formed from sheets or tubes disclosed and described herein.

Referring now to FIGS. 8 and 9, in one embodiment the Nitinol sheet or shape memory alloy from which splines 81 are formed or cut has a thickness ranging between about 0.002 inches and about 0.020 inches, a length ranging between about 2 inches and about 10 inches, and a width ranging between about 2 inches and 10 inches. Among other things, the particular dimensions of the sheet will depend upon the size of the basket structure 83 that is to be formed. In some embodiments, the widths of the individual splines formed from the sheet of Nitinol range between about 0.005 inches and about 0.040 inches, the lengths of the individual splines range between about 2 inches and about 8 inches (depending, again, on the desired dimensions of the basket structure 83). These same dimensions and specifications can also be applied to embodiments basket structures 83 formed from a single tube (as discussed below in connection with FIGS. 11 and 12).

Suitable Nitinol metal or metal alloy sheets or tubes for forming at least some embodiments of basket structure 83 may be obtained from Fort Wayne Metals of Fort Wayne, Ind., and Ulbrich Stainless Steels & Special Metals, Inc. having headquarters in North Haven, Conn. In some embodiments, by way of non-limiting illustrative example, where for example 64 electrodes are disposed on basket structure 83, inter-electrode spacing along splines 81 ranges between about ⅛ of an inch and about ¾ of an inch. Other inter-electrode spacings and numbers of electrodes are also contemplated, as those skilled in the art will now understand. In some embodiments, the diameter of basket structure 83 in a fully deployed and open state can be about 40 mm, 50 mm, 60 mm or 70 mm, depending on the particular application and type of patient at hand. Other basket structure diameters are also contemplated.

Moreover, individual flex circuits containing electrical conductors and electrodes 82 may be disposed on or attached to splines 83, using for example, heat-shrink tubing, polymeric coverings, adhesives, polymeric layers or tubes reflowed down upon the flex circuits and the splines 81, or other techniques known in the art for attaching flex circuits to splines 81, Such flex circuits can also be formed to curve and correspond to the shapes and curves of splines 81, such as by way of non-limiting example, the types of curves and shapes shown in FIGS. 8 through 10b. Alternatively, individual electrodes, such as ring or pad electrodes, and corresponding wire electrical conductors, can be attached to splines 81.

In some embodiments, the vertical edges of collar or attachment member 99 are wrapped around to meet one another and are welded together when basket structure 83 is being formed from the flat structures shown in FIGS. 8 and 9. In one embodiment, the top or distal-most portion of collar or attachment member 99 ranges between about 0.110 inches in diameter, and the bottom or most proximal portion of collar 99 is as small as about 0.050 inches in diameter so that the collar or attachment member can fit inside the distal end of a steerable introducer sheath or a distal end of a catheter body. In some embodiments, collar or attachment member 99 may be attached to a distal portion or end of catheter body 2 using one or more of an adhesive, a reflowed polymer, crimping, welding or swaging. In embodiments where basket structure 83 is to fit inside an outer sheath prior to deployment in a patient's heart, basket structure 83 and collar or attachment member 99 must fit inside such a sheath. An illustrative example of such a sheath is the AGILIS NxT Steerable Introducer and Sheath, which in one embodiment has an inner diameter of 8.5 French (within which the proximal end of collapsed basket structure 83 must fit).

In accordance with FIGS. 8 through 10b, some embodiments of methods of making a cardiac mapping catheter configured for electrophysiological mapping and suitable for intravascular insertion in a patient's heart are now described and disclosed herein. Such methods can include, but are not limited to: (a) cutting Nitinol splines 81 from a single sheet of Nitinol or shape memory alloy disposed or located on a flat or substantially flat surface during cutting; (b) cutting each spline 81 from the sheet such that at its proximal end part 95 each spline 81 terminates in a collar or attachment member 99 contiguous with the proximal end part 95 of the spline 81; (c) cutting the collar or attachment member 99 from the same sheet of Nitinol or shape memory alloy as the splines 81; (d) cutting each spline 81 from the flat or substantially flat sheet such that between its proximal end part 95 and its distal end part 94 each spline 81 forms a series of compound or connected single curves or arcs 107, 108, and 109 that curve first in a first general direction 101 and then curve second in a second general direction 102 opposite or partially opposite to or from the first direction 101. The distal end parts 94 of the splines 81 form separate distal ends 93 that are not connected to one another. The splines 81 are nested together on the flat or substantially flat surface while the curves 107, 108, and 109 in the splines 81 are being cut such that the splines 81 are adjacent to one another and are separated from adjoining splines by continuous intervening spaces 105 formed between the proximal end parts 95 and the distal ends 93 of the splines 81 during cutting. The collar or attachment member 99 is configured, after cutting, to be joined, attached, or secured to the distal portion or distal end 3 of the elongated body 2, or in another embodiment to a distal tip 6 of the basket structure (in which case the distal ends 93 are reversed in position and attached to the distal portion or distal end 3 of the elongated body 2).

After the splines 81 have been formed from the sheet, after the collar 99 has been attached to the distal portion or distal end 3 of the elongated body 2, and after the distal ends 93 of the splines 81 have been attached or secured to the distal tip 6, the basket structure 83 forms a series of spirally winding or spirally wrapping support arms 81 when deployed in the second expanded condition. See FIGS. 10a and 10b. The basket structure 83 and electrodes 82 are thus configured to prevent bunching and promote spacing apart of adjoining support arms 81 when the expanded basket structure 83 is deployed inside a patient's heart in the expanded second condition.

Several different methods of cutting splines 81 and collar or attachment member 99 from a single sheet or tube of Nitinol may be employed. Spaces 105 can be cut, by way of non-limiting example, using well known laser cutting, laser machining; laser etching, high pressure water jet, mechanical cutting, mechanical abrading, chemical etching and dissolution (along with corresponding masking techniques), stamping, coining, milling, grinding plunge or wire EDM, electro-polishing, and other techniques. Other examples of laser techniques for cutting or forming splines 81 and basket structure from a sheet or tube of Nitinol or other shape memory alloy include $CO_2$, Nd, Nd:YAG, Fiber, UV, Excimer, Femtosecond, and/or Picosecond laser cutting or etching methods and techniques.

In another embodiment, and as averred to above, a tube of Nitinol or other suitable shape memory alloy instead of a sheet of Nitinol or other suitable shape memory alloy is employed to form splines 81 and basket structure 83. As shown in the embodiment of tube/yet-to-be basket structure 83 of FIG. 11, cuts or slits 105 are formed in the Nitinol or shape memory alloy tube that extend a distance D just short of the distal end of the tube to the proximal end of the tube to form, by way of non-limiting example, eight splines 81, all splines 81 being contiguous at their distal ends with the top ring or collar 6. Once the slits or cuts 105 have been formed in the Nitinol or shape memory alloy tube, the proximal and/or distal ends of the tube can be compressed to cause the resulting Nitinol splines to bow outwardly and form a basket structure 83. The distal ring or collar 6 shown in FIG. 12 is preferably coated or capped with an atraumatic member or structure to prevent injury to a patient's heart when deployed in situ.

Figure 11:
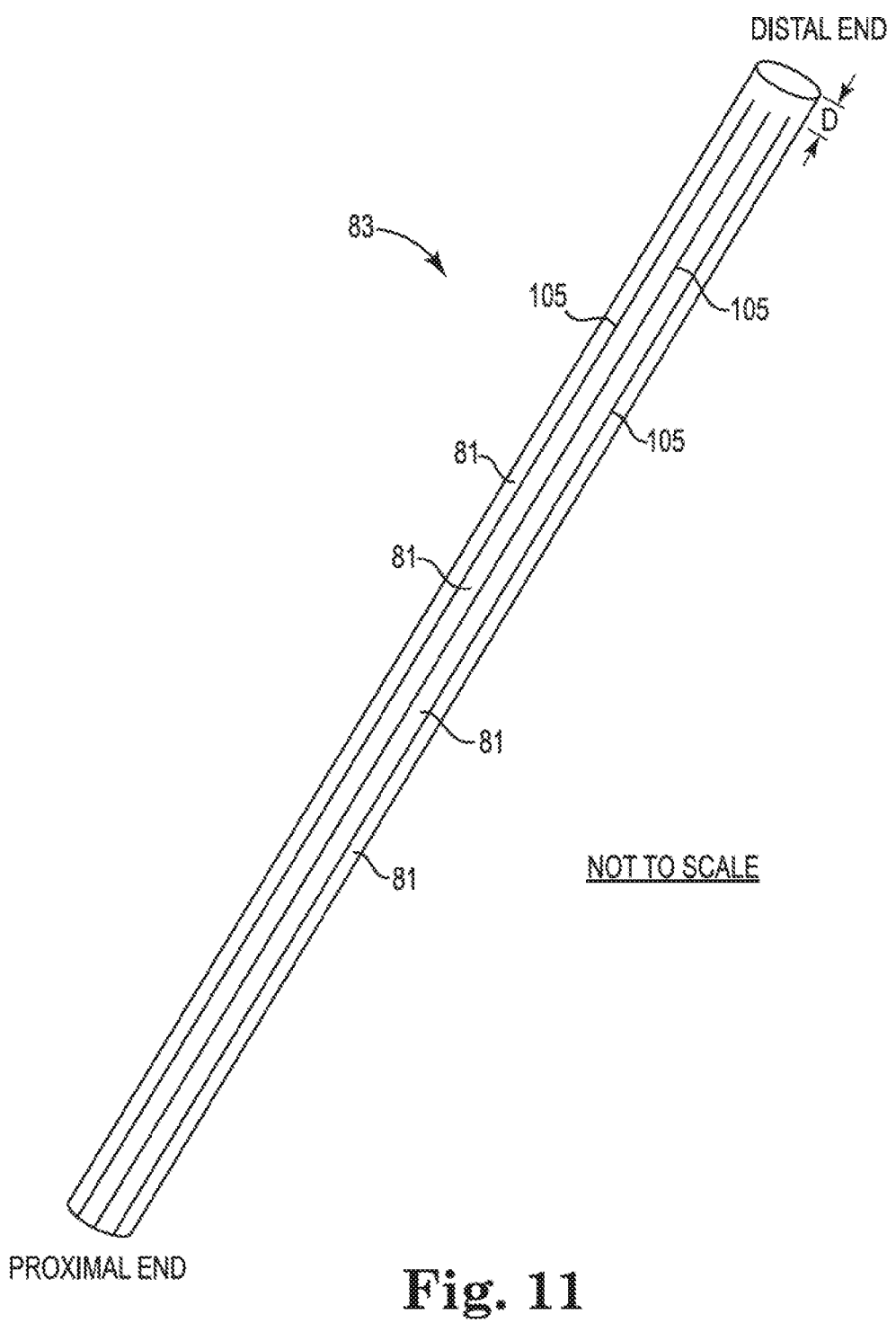
FIG. 11 shows a single tube of Nitinol or shape memory alloy that has been cut to form splines of a basket structure.

After slits 105 have been cut in the tube (as shown in FIG. 11), the resulting structure is placed on a suitable metal or metal alloy heat set tool, which has a suitable shape and dimensions that will provide a basket structure 83 of the desired shape and configuration. The proximal ends of the splines 81 are loaded or placed over, by way of example, a globe- or spherically-shaped metal heat set tool such that the distal end of structure 83 shown in FIG. 11 is located at a top end of the heat set tool, and the proximal ends of the splines are drawn or pulled or located down towards a bottom end of the heat set tool where they are mechanically constrained against the heat set tool by, for example, wires, a confining collar, metal bands or vices, or the like. The splines are positioned and drawn against the outer surface of the heat set tool to form and retain a desired basket shape after a heat setting operation has been carried out. Such a shape can be egg-shaped, football-shaped, spherical, or any other suitable three-dimensional shape that is determined to be desirable or optimal for deployment inside a patient's heart chamber.

The heat set tool with the splines drawn and held thereagainst is then placed, by way of example, in a salt heat bath at a temperature of about 900 degrees F. for about 8 minutes. By way of example, at the end of the heat setting operation, a Nitinol or shape memory alloy basket structure 83 having a configuration such as that shown in FIG. 12 results. Other temperatures, durations, and types of heat setting environments or techniques suitable for Nitinol or other shape memory alloys are also contemplated, such as temperatures between about 750 degrees F. and about 1,500 degrees F., and lengths of time ranging between about 2 minutes and about 30 minutes, between about 4 minutes and about 15 minutes, and between about 6 minutes and about 10 minutes.

The heat setting steps and techniques described above are applied to the embodiments of basket structure 83 shown in FIGS. 6a through 10. Indeed, such heat setting steps are necessary so that the proper or desired shape of Nitinol or shape memory alloy basket structure 83 in its deployed or open state may be imparted thereto.

Figure 12:
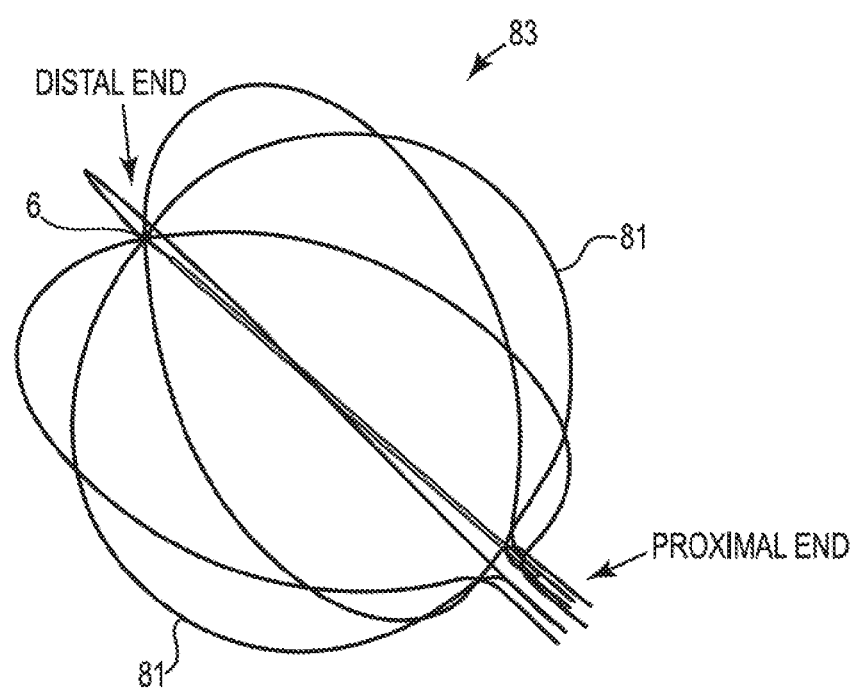
FIG. 12 shows one embodiment of a basket structure that has been formed from the single tube of Nitinol or shape memory alloy of FIG. 11 after the cut tube has been heat set to form the basket structure.

In one embodiment, after heat setting has been applied to basket structure 83, the proximal end parts of splines 81 shown in FIGS. 11 and 12 are attached or secured to the distal portion or distal end of flexible elongated body 2 by pushing, positioning or securing a ferrule or pin down inside the distal end of elongated body 2 so that the proximal ends of splines 81 are forced against and held to the inner diameter of flexible elongated body 2 thereby. Other means of attaching the proximal ends of splines 81 to the distal end or distal portion of flexible elongated elongated body 2 are also contemplated, such as using adhesives, welds, crimps, swages, and the like.

Using a Nitinol tube to form a basket structure 83 has several advantages, including reducing the number of steps required to form a Nitinol basket structure 83, and requiring less Nitinol metal from which to form basket structure 83. Such a basket structure 83 formed from a Nitinol tube can comprise straight or uncurved splines, or can comprise curved splines that form a spirally wound or wrapped basket structure configuration. An atraumatic tip can be attached to the distal end of the resulting cut or slit tube to protect the patient's heart when the basket structure 83 is deployed.

Note that according to various embodiments the proximal and distal ends of splines 81 shown in basket structures 83 disclosed in FIGS. 6a through 12, where the splines are cut from a single sheet or tube of Nitinol or shape memory alloy, may be reversed, as may collars, rings, or attachment members 99.

What have been described above are examples and embodiments of the devices and methods described and disclosed herein. It is, of course, not possible to describe every conceivable combination of components or methodologies for purposes of describing the invention, but one of ordinary skill in the art will recognize that many further combinations and permutations of the devices and methods described and disclosed herein are contemplated and possible. Accordingly, the devices and methods described and disclosed herein are intended to embrace all such alterations, modifications and variations that fall within the scope of the appended claims. In the claims, unless otherwise indicated, the article "a" is to refer to "one or more than one."

The foregoing outlines features of several embodiments so that those skilled in the art may better understand the detailed description set forth herein. Those skilled in the art will now understand that many different permutations, combinations and variations of the basket catheters will fall within the scope of the various embodiments. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

After having read and understood the present specification, those skilled in the art will now understand and appreciate that the various embodiments described herein provide solutions to long-standing problems, both in the use of electrophysiological mapping systems and in the use of cardiac ablation systems.

We claim:

1. A cardiac mapping catheter configured for electrophysiological mapping and suitable for intravascular insertion in a patient's heart, the catheter comprising a flexible elongated body having a distal portion with a distal end and a proximal portion, and an electrode assembly located at the distal portion, the electrode assembly comprising a plurality of support arms, each support arm having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition wherein the plurality of support arms is arranged in a collapsed bundle, and a second expanded condition wherein the plurality of support arms forms an expanded basket structure, at least one of two or more neighboring distal end parts and two or more neighboring proximal end parts being combined, attached to one another, or held together with one or more combining means, members or structures, and wherein the combining means, members or structures further are configured to act as or comprise at least one of stiffening, directionally biased, movement-limiting, rotation-limiting, and twisting-limiting means, members or structures, such stiffening means, members or structures being configured to prevent bunching and promote spacing apart of adjoining support arms when the expanded basket structure is deployed inside a patient's heart in the expanded second condition, and further wherein at least one of the distal end parts and the proximal end parts of at least some supporting members are not combined or held together with combining means, members or structures.

2. The cardiac mapping catheter of claim 1, wherein the stiffening, directionally biased, movement-limiting, rotation-limiting, and twisting-limiting means, members or structures comprise one or more of V- or U-shaped elements.

3. The cardiac mapping catheter of claim 2, wherein the V- or U-shaped elements form opposing legs attached to adjoining but different support arms of the basket structure.

4. The cardiac mapping catheter of claim 3, wherein the V- or U-shaped elements correspond to at least one of pairs of elements oriented such that their open ends point upwardly from the proximal end of the basket structure towards the distal end of the basket structure, and pairs of elements oriented such that their open ends point downwardly from the distal end of the basket structure towards the proximal end of the basket structure.

5. The cardiac mapping catheter of claim 1, wherein at least one of the support arms and combining means are together configured such that one support arm cannot be deflected or bent towards a neighboring support arm by an angle exceeding $\beta$ when the at least one support arms is in contact with a surface, the angle $\beta$ ranging between about 5° and about 30°.

6. The cardiac mapping catheter of claim 1, wherein at least one of the combining means, members or structures and the stiffening means, members or structures comprise one or more of clamping elements, clamps, polymeric, elastomeric, adhesive, metal, metal alloy, foil, wire, woven, carbon fiber or carbon fiber layer combining or stiffening means, members r structures, covers, sheaths, overmoldings, tubing, shrink tubing, ring members, rings, adhesive elements, lugs, welds, stakes, staples, crimps, polymeric, plastic metal, or metal alloy stiffening members, or any combination of the foregoing.

7. The cardiac mapping catheter of claim 1, wherein at least one of the support arms comprises a Nitinol spline having electrodes mounted thereon or attached thereto, or at least one of the support arms comprises a flexible electrical polymeric sheet or flex circuit comprising electrodes and associated circuitry.

8. The cardiac mapping catheter of claim 1, wherein the number of support arms equals 4, 6, 8, 10 or 12.

9. The cardiac mapping catheter of claim 1, wherein the number of electrodes disposed on each support arm ranges between 4 electrodes and 24 electrodes.

10. The cardiac mapping catheter of claim 1, wherein the plurality of electrodes disposed on each support arm is distributed spatially substantially evenly thereon.

11. The cardiac mapping catheter of claim 10, wherein in the expanded condition each of the support arms spans a curve of about 180° between the two pole areas P1 and P2.

12. The cardiac mapping catheter of claim 10, wherein an angle α defines a circumferential distance along a support arm from at least one of the poles P1 and P2 to a boundary between at least one of the proximal and distal end parts of the support arm and the central or main part of the support arm, the angle α ranges between about 5° and about 40°, and no electrodes are disposed along the circumferential distance or distances defined by the angle α.

13. The cardiac mapping catheter of claim 12, wherein the angle α ranges between about 5° and about 30°.

14. The cardiac mapping catheter of claim 1, wherein the basket structure comprises two pole areas P1 and P2 that lie along a basket axis A.

15. A method of making a cardiac mapping catheter configured for electrophysiological mapping and suitable for intravascular insertion in a patient's heart, the method comprising:
forming a flexible elongated body having a distal portion with a distal end and a proximal portion, and
forming an electrode assembly located at the distal portion, the electrode assembly comprising a plurality of support arms, each support arm having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition, where the plurality of support arms is arranged in a collapsed bundle, and a second expanded condition, where the plurality of support arms forms an expanded basket structure, at least one of two or more neighboring distal end parts and two or more neighboring proximal end parts being combined, attached to one another, or held together with one or more combining means, members or structures;
wherein the combining means, members or structures further are configured to act as or comprise at least one of stiffening, directionally biased, movement-limiting, rotation-limiting, and twisting-limiting means, members or structures, such stiffening means, members or structures being configured to prevent bunching and promote spacing apart of adjoining support arms when the plurality of support arms and the expanded basket structure is deployed inside a patient's heart in the expanded second condition, and further wherein at least one of the distal end parts and the proximal end parts of at least some supporting members are not combined or held together with combining means, members or structures.

16. The method of claim 15, further comprising forming at least one of the combining means, members or structures and the stiffening means, members or structures from one or more of clamping elements, clamps, polymeric, elastomeric, adhesive, metal, metal alloy, foil, wire, woven, carbon fiber or carbon fiber layer combining or stiffening means, members r structures, covers, sheaths, overmoldings, tubing, shrink tubing, ring members, rings, adhesive elements, lugs, welds, stakes, staples, crimps, polymeric, plastic metal, or metal alloy stiffening members, or any combination of the foregoing.

17. A cardiac mapping catheter configured for electrophysiological mapping and suitable for intravascular insertion in a patient's heart, the catheter comprising a flexible elongated body having a distal portion with a distal end and a proximal portion, and an electrode assembly located at the distal portion, the electrode assembly comprising a plurality of support arms comprising Nitinol or shape memory alloy splines, each spline having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition, where the plurality of support arms is arranged in a collapsed bundle, and a second expanded condition, where the plurality of support arms forms an expanded basket structure, wherein the Nitinol or shape memory alloy splines are cut from a single sheet of Nitinol or shape memory alloy disposed or located on a flat or substantially flat surface during cutting, each spline being cut from the sheet such that at its proximal end part each spline terminates in an attachment member contiguous with the proximal end part of the spline, the attachment member being cut from the same sheet of Nitinol or shape memory alloy as the spline, wherein each spline is cut from the flat or substantially flat sheet such that between its proximal end part and its distal end part each spline forms a series of compound curves or arcs that curve first in a first general direction and then curve second in a second general direction opposite or partially opposite to or from that of the first direction, the distal end parts of the splines forming separate distal ends that are not connected to one another, the splines being nested together on the flat or substantially flat surface when the curves in the splines are being cut such that the splines are adjacent to one another and are separated from adjoining splines by continuous intervening spaces formed between the proximal end parts and the distal ends of the splines during cutting, the attachment member being configured, after cutting, to be joined, attached, or secured to the distal portion or distal end of the elongated body or to a distal tip of the basket structure, and further wherein after the splines have been formed from the sheet, after the collar has been attached to the distal portion or distal end of the elongated body, and after the distal ends of the splines have been attached or secured to the distal tip, the basket structure forms a series of spirally winding or spirally wrapping support arms when deployed in the second expanded condition, the basket structure and electrodes being configured to prevent bunching and promote spacing apart of adjoining support arms when the expanded basket structure is deployed inside a patient's heart in the expanded second condition.

18. A method of making a cardiac mapping catheter configured for electrophysiological mapping and suitable for intravascular insertion in a patient's heart, the catheter comprising a flexible elongated body having a distal portion with a distal end and a proximal portion, and an electrode assembly located at the distal portion, the electrode assembly comprising a plurality of support arms comprising Nitinol or shape memory alloy splines, each spline having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition, where the plurality of support arms is arranged in a collapsed bundle, and a second expanded condition, where the plurality of support arms forms an expanded basket structure, the method comprising:
cutting the Nitinol splines from a single sheet of Nitinol or shape memory alloy disposed or located on a flat or substantially flat surface during cutting;
cutting each spline from the sheet such that at its proximal end part each spline terminates in an attachment member contiguous with the proximal end part of the spline;
cutting the attachment member from the same sheet of Nitinol or shape memory alloy as the spline;
cutting each spline from the flat or substantially flat sheet such that between its proximal end part and its distal end part each spline forms a series of compound curves or arcs that curve first in a first general direction and then curve second in a second general direction opposite or partially opposite to or from the first direction, the distal end parts of the splines forming separate distal ends that are not connected to one another, the splines being nested together on the flat or substantially flat surface while the curves in the splines are being cut such that the splines are adjacent to one another and are separated from adjoining splines by continuous intervening spaces formed between the proximal end parts and the distal ends of the splines during cutting, and
configuring the attachment member, after cutting, to be joined, attached, or secured to the distal portion or distal end of the elongated body or to a distal tip of the basket structure;
wherein after the splines have been formed from the sheet, after the attachment member has been attached to the distal portion or distal end of the elongated body, and after the distal ends of the splines have been attached or secured to the distal tip, the basket structure forms a series of spirally winding or spirally wrapping support arms when deployed in the second expanded condition, the basket structure and electrodes being configured to prevent bunching and promote spacing apart of adjoining support arms when the expanded basket structure is deployed inside a patient's heart in the expanded second condition.

19. A cardiac mapping catheter configured for electrophysiological mapping and suitable for intravascular insertion in a patient's heart, the catheter comprising a flexible elongated body having a distal portion with a distal end and a proximal portion, and an electrode assembly located at the distal portion, the electrode assembly comprising a plurality of support arms comprising Nitinol or shape memory alloy splines, each spline having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition, where the plurality of support arms is arranged in a collapsed bundle, and a second expanded condition, where the plurality of support arms forms an expanded basket structure, wherein the Nitinol or shape memory alloy splines are cut from a single tube of Nitinol or shape memory alloy, each spline being formed or cut from the tube such that at its distal end part each spline terminates in a ring or collar contiguous with the distal end part of the spline, the ring or collar being cut from the same tube of Nitinol or shape memory alloy as the splines and forming a distal portion of the basket structure, the proximal end parts of the splines forming separate proximal ends that are not connected to one another after being cut from the tube, the proximal ends of the splines being configured, after cutting, to be joined, attached, or secured to the distal portion or distal end of the elongated body, and further wherein after the splines have been formed from the tube, and after the proximal ends of the splines have been attached or secured to the distal portion or the distal end part of the flexible elongated body, the basket structure comprises a plurality of outwardly bowing or curved splines when deployed in the second expanded condition.

20. A method of making a cardiac mapping catheter configured for electrophysiological mapping and suitable for intravascular insertion in a patient's heart, the catheter comprising a flexible elongated body having a distal portion with a distal end and a proximal portion, and an electrode assembly located at the distal portion, the electrode assembly comprising a plurality of support arms comprising Nitinol or shape memory alloy splines, each spline having a proximal end part, a distal end part, and a main part located between the proximal end part and the distal end part, each of the plurality of support arms comprising a plurality of electrodes, the electrodes being configured to acquire electrophysiological signals from the patient's heart, the plurality of support arms being configured to have a first retracted condition, where the plurality of support arms is arranged in a collapsed bundle, and a second expanded condition, where the plurality of support arms forms an expanded basket structure, the method comprising:
cutting the Nitinol splines from a single tube of Nitinol or shape memory alloy;
cutting each spline from the tube such that at its distal end part each spline terminates in a collar or ring contiguous with the distal end part of the spline, the collar or ring being cut from the same tube of Nitinol or shape memory alloy as the splines;
further cutting each spline from the tube such the proximal end parts of each spline not connected to one another, and
joining, attaching, or securing the proximal end parts of the splines to the distal portion or distal end of the elongated body;
wherein after the splines have been formed from the tube, after the proximal end parts of the splines have been joined, attached, or secured to the distal portion or distal end of the elongated body, the basket structure comprises a plurality of outwardly bowing or curved splines when deployed in the second expanded condition.

\* \* \* \* \*